(12) United States Patent
Spirig et al.

(10) Patent No.: US 10,973,891 B2
(45) Date of Patent: Apr. 13, 2021

(54) TREATMENT AND PREVENTION OF REMOTE ISCHEMIA-REPERFUSION INJURY

(71) Applicants: CSL Behring GmbH, Marburg (DE); Universitaet Bern, Bern (CH)

(72) Inventors: Rolf Spirig, Bern (CH); Sylvia Miescher, Bern (CH); Marc Nolte, Marburg (DE); Claudia Duehrkop-Sisewitsch, Knivsta (SE); Robert Rieben, Hinterkappelen (CH)

(73) Assignees: CSL Behring GmbH, Marburg (DE); Universitaet Bern, Bern (CH)

(*) Notice: Subject to any disclaimer, the term of this patent is extended or adjusted under 35 U.S.C. 154(b) by 0 days.

(21) Appl. No.: 16/359,598

(22) Filed: Mar. 20, 2019

(65) Prior Publication Data

US 2019/0269766 A1 Sep. 5, 2019

Related U.S. Application Data

(62) Division of application No. 14/773,020, filed as application No. PCT/EP2014/054489 on Mar. 7, 2014, now Pat. No. 10,286,047.

(30) Foreign Application Priority Data

Mar. 8, 2013 (EP) ..................................... 13158478

(51) Int. Cl.
| | | |
|---|---|---|
| C07K 14/745 | (2006.01) | |
| A61K 38/36 | (2006.01) | |
| A61P 7/04 | (2006.01) | |
| A61K 38/57 | (2006.01) | |
| A61K 45/06 | (2006.01) | |

(52) U.S. Cl.
CPC .............. *A61K 38/57* (2013.01); *A61K 38/36* (2013.01); *A61K 45/06* (2013.01); *A61P 7/04* (2018.01); *C07K 14/745* (2013.01)

(58) Field of Classification Search
CPC combination set(s) only.
See application file for complete search history.

(56) References Cited

U.S. PATENT DOCUMENTS

| | | |
|---|---|---|
| 4,383,219 A | 5/1983 | Kaplan |
| 4,915,945 A | 4/1990 | Pelzer et al. |
| 5,252,714 A | 10/1993 | Harris et al. |
| 5,380,299 A | 1/1995 | Fearnot et al. |
| 5,939,389 A | 8/1999 | Eisele et al. |
| 6,090,777 A | 7/2000 | Hack et al. |
| 6,248,365 B1 | 6/2001 | Römisch et al. |
| 6,403,077 B1 | 6/2002 | Strom et al. |
| 6,613,890 B2 | 9/2003 | White et al. |
| 7,053,176 B1 | 5/2006 | Häfner et al. |
| 7,083,784 B2 | 8/2006 | Dall'Acqua et al. |
| 8,071,532 B2 | 12/2011 | Mannesse et al. |
| 8,283,319 B2 | 10/2012 | Schulte et al. |
| 9,352,016 B2 | 5/2016 | Zeitler et al. |
| 9,518,127 B2* | 12/2016 | Panousis ................ C07K 16/40 |
| 9,624,307 B2 | 4/2017 | Nahrendorf et al. |
| 9,856,325 B2 | 1/2018 | Panousis et al. |
| 9,856,326 B2 | 1/2018 | Panousis et al. |
| 9,957,329 B2 | 5/2018 | Meuth et al. |
| 9,987,328 B2 | 6/2018 | Zeitler et al. |
| 10,286,047 B2 | 5/2019 | Spirig et al. |
| 10,471,142 B2 | 11/2019 | Basta et al. |
| 2003/0219430 A1 | 11/2003 | Faerman et al. |
| 2004/0015104 A1 | 1/2004 | Goldberger |
| 2004/0087778 A1 | 5/2004 | Feige et al. |
| 2005/0059660 A1 | 3/2005 | Fox et al. |
| 2005/0060028 A1 | 3/2005 | Horres et al. |
| 2005/0176108 A1 | 8/2005 | Kim et al. |
| 2006/0024745 A1 | 2/2006 | Pritchard |
| 2006/0148901 A1 | 7/2006 | Sturzebecher et al. |
| 2007/0135620 A1 | 6/2007 | Chamberlain et al. |
| 2007/0196367 A1 | 8/2007 | Dinu |
| 2008/0254039 A1 | 10/2008 | Nieswandt et al. |
| 2009/0233852 A1 | 9/2009 | Blair et al. |
| 2010/0143325 A1 | 6/2010 | Gurewich |
| 2010/0143344 A1 | 6/2010 | Baas et al. |
| 2010/0317848 A1 | 12/2010 | Han et al. |
| 2010/0330071 A1 | 12/2010 | Teschner et al. |
| 2012/0088728 A1 | 4/2012 | Mannesse et al. |
| 2012/0189626 A1 | 7/2012 | Ashkenazi et al. |

(Continued)

FOREIGN PATENT DOCUMENTS

| | | |
|---|---|---|
| EP | 0 154 316 B1 | 9/1989 |
| EP | 0 401 384 A1 | 12/1990 |

(Continued)

OTHER PUBLICATIONS

Tekin et al., "Antithrombin III prevent deleterious effects of remote ischemia-reperfusion injury on healing of colonic anastomoses", The American Journal of Surgery, 2002, 160-165 (Year: 2002).*
Molina et al. "Extending Reperfusion Therapy for Acute Ischemic Stroke: Emerging Pharmacological, Mechanical and Imaging Strategies", Stroke, 2005, 2311-2320 (Year: 2005).*
Aytekin et al., "Antithrombin III attenuates pulmonary tissue injury caused by mesenteric ischemia-reperfusion", The American Journal of Surgery, 2005, 161-166 (Year: 2005).*
Achiron et al. (Feb. 1998) "Intravenous immunoglobulin treatment in multiple sclerosis: Effect on relapses" *Neurol.*, 50:398-402.
Adams Jr, H.P. (2003) "Stroke: a vascular pathology with inadequate management" *J Hypertens*, 21 (Suppl 5):S3-S7.

(Continued)

*Primary Examiner* — Lianko G Garyu
(74) *Attorney, Agent, or Firm* — Finnegan, Henderson, Farabow, Garrett & Dunner, LLP

(57) ABSTRACT

The present invention relates to a contact activation system inhibitor, preferably a C1INH, for use in the treatment and/or prevention of remote ischemia-reperfusion injury (IRI), comprising administering the contact activation system inhibitory to an individual.

21 Claims, 7 Drawing Sheets
Specification includes a Sequence Listing.

(56) References Cited

U.S. PATENT DOCUMENTS

| | | | |
|---|---|---|---|
| 2014/0072572 A1 | 3/2014 | Nahrendorf et al. |
| 2014/0072600 A1 | 3/2014 | Zeitler et al. |
| 2014/0199361 A1 | 7/2014 | Panousis et al. |
| 2014/0234293 A1 | 8/2014 | Basta et al. |
| 2014/0378653 A1 | 12/2014 | Meuth et al. |
| 2016/0166660 A1 | 6/2016 | Nolte et al. |
| 2016/0279195 A1 | 9/2016 | Zeitler et al. |
| 2019/0309089 A1 | 10/2019 | Panousis et al. |
| 2020/0129600 A1 | 4/2020 | Nolte et al. |

FOREIGN PATENT DOCUMENTS

| | | | | |
|---|---|---|---|---|
| EP | 0 952 215 A2 | 10/1999 | | |
| EP | 2 497 489 A1 | 9/2012 | | |
| JP | 57-14358 A | 1/1982 | | |
| JP | 11-209399 A | 8/1999 | | |
| JP | 2001-276217 A | 10/2001 | | |
| JP | 2002-508953 A | 3/2002 | | |
| JP | 2010-505946 A | 2/2010 | | |
| JP | 2010-518039 A | 5/2010 | | |
| WO | WO 89/11865 A1 | 12/1989 | | |
| WO | WO 90/08835 A1 | 8/1990 | | |
| WO | WO 91/17258 A1 | 11/1991 | | |
| WO | WO 92/16221 A1 | 10/1992 | | |
| WO | WO 95/34326 A1 | 12/1995 | | |
| WO | WO 97/07731 A2 | 3/1997 | | |
| WO | WO 97/42873 A1 | 11/1997 | | |
| WO | WO 99/36439 A1 | 7/1999 | | |
| WO | WO 2001/79271 A1 | 10/2001 | | |
| WO | WO 2003/065881 A2 | 8/2003 | | |
| WO | WO 2003/076567 A2 | 9/2003 | | |
| WO | WO 2004/075837 A2 | 9/2004 | | |
| WO | WO 2004/100982 A1 | 11/2004 | | |
| WO | WO 2004/101740 A2 | 11/2004 | | |
| WO | WO 2005/000892 A2 | 1/2005 | | |
| WO | WO 2005/001025 A2 | 1/2005 | | |
| WO | WO 2005/024044 A2 | 3/2005 | | |
| WO | WO 2005/063808 A1 | 7/2005 | | |
| WO | WO 2006/000448 A2 | 1/2006 | | |
| WO | WO 2006/033386 A1 | 3/2006 | | |
| WO | WO 2006/066878 A1 | 6/2006 | | |
| WO | WO 2007/073186 A2 | 6/2007 | | |
| WO | WO-2007073186 A2 * | 6/2007 | ............. | A61K 38/57 |
| WO | WO 2007/112986 A1 | 10/2007 | | |
| WO | WO 2007/122371 A1 | 11/2007 | | |
| WO | WO 2008/044928 A1 | 4/2008 | | |
| WO | WO 2008/091692 A2 | 7/2008 | | |
| WO | WO 2008/098720 A1 | 8/2008 | | |
| WO | WO 2009/067660 A2 | 5/2009 | | |
| WO | WO 2010/049423 A1 | 5/2010 | | |
| WO | WO 2010/080538 A1 | 7/2010 | | |
| WO | WO 2010/085682 A2 | 7/2010 | | |
| WO | WO 2013/014092 A1 | 1/2013 | | |
| WO | WO-2013014092 A1 * | 1/2013 | ............. | C07K 16/36 |

OTHER PUBLICATIONS

Adeoye, O. et al. (2011) "Recombinant Tissue-Type Plasminogen Activator Use for Ischemic Stroke in the United States" *Stroke* 42(7):1952-1955.

Akita, N. et al. (2001) "The effect of C 1 esterase inhibitor on ischemia: reperfusion injury in the rat brain" *No To Shinkei*, 53:641-644. English language abstract, p. 644.

Akita, N. et al. (Feb. 2003) "Protective Effective of C1 Esterase Inhibitor on Reperfusion Injury in the Rat Middle Cerebral Artery Occlusion Model" *Neurosurgery*, 52(2):395-401.

Alonso, A. and M.A. Hernan (2008) "Temporal Trends in the Incidence of Multiple Sclerosis" *Neurology*, 71:129-135.

Altschul, S.F. et al. (1990) "Basic Local Alignment Search Tool" *J. Mol. Biol.*, 215:403-410.

Armour, K.L. et al. (1999) "Recombinant human IgG molecules lacking Fcγ receptor I binding and monocyte triggering activities" *Eur. J. Immunol.*, 29:2613-2624.

Arumugam, T. et al. (Aug. 28, 2007) "Intravenous immunoglobulin (IVIG) protects the brain against experimental stroke by preventing complement-mediated neuronal cell death" *Proc. Natl. Acad. Sci. USA*, 104(35):14104-14109.

Arumugam, T. et al. (2008) "Targeting ischemic brain injury with intravenous immunoglobulin" *Exp. Opin. Ther. Targets*, 12(1):19-29.

Arumugam, T. et al. (2009) "Neuroprotection in Stroke by Complement Inhibition and Immunoglobulin Therapy" *Neuroscience*, 158(3):1074-1089.

Australian Patent Application No. 2012289001: Examination Report, dated Aug. 15, 2014; 7 pages.

Australian Patent Application No. 2012311483: Examination Report, dated Jul. 29, 2014; 4 pages.

Bauer, T.L. et al. (1997) "Prevalence of Heparin-Associated Antibodies Without Thrombosis in Patients Undergoing Cardiopulmonary Bypass Surgery" *Circulation*, 95:1242-1246.

Beattie, W. and A. Dugalczyk (1982) "Structure and evolution of human α-fetoprotein deduced from partial sequence of cloned cDNA" *Gene*, 20:415-422.

Bendszus, M. (Oct. 4, 2004) "Heparin and Air Filters Reduce Embolic Events Caused by Intra-Arterial Cerebral Angiography. A Prospective, Randomized Trial" *Circulation*, 110:2210-2215.

Bendszus, M. and G. Stoll (2006) "Silent cerebral ischaemia: hidden fingerprints of invasive medical procedures" *Lancet Neurol*, 5:364-372.

Bendszus, M. et al. (Nov. 6, 1999) "Silent embolism in diagnostic cerebral angiography and neurointerventional procedures: a prospective study" *Lancet*, 354(9190):1594-1597.

Bergamaschi, R. et al. (2006) "Disability and Mortality in a Cohort of Multiple Sclerosis Patients: A Reappraisal" *Neuroepidemiology*, 25:15-18.

Berinert® FDA package insert, revised Feb. 2014.

Bettini, R. and D. Cocconi (2001) Book review of: *Handbook of Pharmaceutical Excipients*. Third Edition. Arthur H. Kibbe (ed.), London: Pharmaceutical Press, 2000; in *J. Controlled Release*, 71:352-353.

Brea, D. et al. (2011) "Toll-like receptors 2 and 4 in ischemic stroke: outcome and therapeutic values" *J Cerebral Blood Flow & Metabolism*, 31:1424-1431.

Breckwoldt, M.O. et al. (Nov. 25, 2008) "Tracking the inflammatory response in stroke in vivo by sensing the enzyme myeloperoxidase" *PNAS*, 105(47):18584-18589.

Briguori, C. et al. (1999) "Administration of protamine after coronary stent deployment" *Am Heart J*, 138:64-68.

Brodsky, R. (Ed.) (2006) "Multiple Sclerosis" Gale Encyclopedia of Medicine, 3rd Edition; [online]. Encyclopedia.com, 13 pages; accessed Sep. 7, 2016.

Buchwald, A.B. et al. (Jan. 1993) "Platelet and Fibrin Deposition on Coronary Stents in Minipigs: Eftect of Hirudin Versus Heparin" *J Am Coll Cardiol*, 21(1):249-254.

Burke, B. et al., "Transgenic Mice Showing Inflammation-Inducible Overexpression of Granulocyte Macrophage Colony-Stimulating Factor," *Clinical and Diagnostic Laboratory Immunology*, 2004, 11(3): 588-598.

Campos, I.T.N. et al. (2002) "Infestin, a thrombin inhibitor presents in *Triatoma infestans* midgut, a Chagas' disease vector: gene cloning, expression and characterization of the inhibitor" *Insect Biochem Mol Bio*, 32:991-997.

Chamorro, A. et al. (Jul. 2012) "The immunology of acute stroke" *Neurology*, 8:401-410.

Chen, J. et al., "Transgenic Animals with Inducible, Targeted Gene Expression in Brain," *Molecular Pharmacology*, 1998; 54: 495-503.

Chen, J.W. et al. (2008) "Myeloperoxidase-targeted imaging of active inflammatory lesions in murine experimental autoimmune encephalomyelitis" *Brain*, 131:1123-1133.

Chen, J.W. et al. (2012) "Selective Factor XIIa Inhibition Attenuates Silent Brain Ischemia" *J Am Coll Cardiol Img*, 5(11):1127-1138.

Chen, J.W. et al. (Aug. 2006) "Imaging of Myeloperoxidase in Mice by Using Novel Amplifiable Paramagnetic Substrates" *Radiology*, 240(2):473-481.

(56) References Cited

OTHER PUBLICATIONS

Chen, X. et al. (2011) "Inhibition and Scavenging of Complement as Therapeutic Targets in the Mouse Model of Actue Ischemic Stroke" *Annals Neurol.*, 70(Suppl. 15):S4-S5.

Chen, X. et al. (Nov. 12, 2011) "Therapeutic efficacy of natural inhibitors of the complement cascade in a mouse model of focal ischemic stroke" Presentation Abstract, Society for Neuroscience, vol. 41, Program No. 62.04, Poster No. FFF10.

Chen, Z-Y. et al. (Mar. 1999) "Inhibition of Plant-Pathogenic Fungi by a Corn Trypsin Inhibitor Overexpressed in *Escherichia coil*" *Applied and Environmental Microbiology*, 65(3):1320-1324.

Chinese Patent Application No. 201280012244.0: Notification of the First Office Action, dated Sep. 24, 2014, with English translation; 20 pages.

Chou, K-J. et al. (1997) "Distribution of Antihistamines Into the CSF Following Intranasal Delivery" *Biopharm Drug Dispos*, 18(4):335-346.

Citarella, F. et al. (1996) "Structure/function analysis of human factor XII using recombinant deletion mutants. Evidence for an additional region involved in the binding to negatively charged surfaces" *Eur. J. Biochem.*, 238:240-249.

Claudio, L. et al. (1995) "Evidence of Persistent Blood-Brain Barrier Abnormalities in Chronic-Progressive Multiple Sclerosis" *Acta Neuropathol*, 90:228-238.

Cojocaru, I.M. et al. (2008) "Changes in Plasma Levels of Complement in Patients with Acute Ischemic Stroke" *Rom. J. Intern. Med.*, 46(1):77-80.

Cole et al. (1985) *Monoclonal Antibodies and Cancer Therapy*. Alan R. Liss, Inc., pp. 33-74.

Colman, R.W. et al. (2001) "Contact Activation Pathway: Inflammatory, Fibrinolytic, Anticoagulant, Antiadhesive, and Antiangiogenic Activities" Chapter 6 in *Hemostasis and Thrombosis. Basic Principles and Clinical Practice*. Fourth Edition; Philadelphia, Pennsylvania: Lippincott Williams & Wilkins; pp. 103-121.

Cooke, E. et al. (Dec. 1985) "Serum Vitamin D-binding Protein Is a Third Member of the Albumin and Alpha Fetoprotein Gene Family" *J Clin Invest*, 76:2420-2424.

Culmsee, C. et al. (2004) "Combination Therapy in Ischemic Stroke: Synergistic Neuroprotective Effects of Memantine and Clenbuterol" *Stroke*, 35:1197-1202.

D'Ambrosio, A.L. et al. (2001) "The Role of the Complement Cascade in Ischemia/Reperfusion Injury: Implications for Neuroprotection" *Molecular Medicine*, 7(6):367-382.

Dall'Acqua et al. (2006) "Modulation of the Effector Functions of a Human IgG1 through Engineering of Its Hinge Region" *J. Immunol*, 177:1129-1138.

Database WPI, Thomson (1999) Abstract of Japanese Patent Publication No. JPH11209399; Acc. No. 1999-488816; 1 page.

Davis, et al., 2008. "Biological activities of C1 inhibitor," *Mol Immunol* 45: 4057-4063.

De Keyser, J. et al. (1999) "Clinical trials with neuroprotective drugs in acute ischaemic stroke: are we doing the right thing?" *Trends Neurosci*, 22(12):535-540.

De Keyser, J. et al. (2005) "Neuroprotection in acute ischemic stroke" *Acta Neurol Belg*, 105:144-148.

De Simoni, M.G. et al. (2003) "Neuroprotection by Complement (C1) Inhibitor in Mouse Transient Brain Ischemia" *J Cereb Blood Flow Metab*, 23(2):232-239.

De Simoni, M.G. et al. (May 2004) "The Powerful Neuroprotective Action of C1-Inhibitor on Brain Ischemia-Reperfusion Injury Does Not Require C1q" *Am J Pathol*, 164(5):1857-1863.

Devereux, J. et al. (1984) "A comprehensive set of sequence analysis programs for the VAX" *Nucleic Acids Research*, 12(1):387-395.

Dick, et al., 2008. "Basic control of reperfusion effectively protects against reperfusion injury in a realistic rodent model of acute limb ischemia," *Circulation* 118: 1920-1928.

Dillion, et al., "Hypertonic saline reduces skeletal muscle injury and associated remote organ injury following ischemia reperfusion injury," *Acta Orthopaedica*, 2008, 703-707.

Dors, D.M. et al. (1992) "A Novel Sensitive Assay for Functional Factor XII Based on the Generation of Kallikrein-C1-Inhibitor Complexes in Factor XII-Deficient Plasma by Glass-Bound Factor XII" *Thromb Haemost*, 67(6):644-648.

Draghia, R. et al. (1995) "Gene Delivery into the Central Nervous System by Nasal Instillation in Rats" *Gene Ther*, 2(6):418-423.

Drouet et al., 1988. "A sensitive method to assay blood complement C1-inhibitor activity," *Clin. Chim Acta.* 174(2):121-30.

Drug Commission of the German Medical Association (Apr. 2000) "Schwerwiegende Thrombenbildung nach Berinert® HS (Serious thrombus after Berinert® HS)" Dtsch Arztebl, 97(15):A-1016-A-1023. Machine translated abstract and summary provided by Google, 2 pages.

Duehrkop, C. et al., (2013) "C1 Esterase Inhibitor Reduces Lower Extremity Ischemia/Reperfusion Injury and Associated Lung Damage," *PLOS ONE*, 8(8); e72059 (15 pages).

Dyke, C. et al. (2005) "Preemptive Use of Bivalirudin for Urgent On-Pump Coronary Artery Bypass Grafting in Patients With Potential Heparin-Induced Thrombocytopenia" *Ann Thorac Surg*, 80:299-303.

Edelman, G.M. et al. (1969) "The Covalent Structure of an Entire γG Immunoglobulin Molecule" *PNAS*, 63:78-85.

Edmunds Jr., L.H. and R.W. Colman (2006) "Thrombin During Cardiopulmonary Bypass" *Ann. Thorac. Surg.*, 82:2315-2322.

Esnouf, M.P. et al. (2000) "A Monoclonal Antibody Raised against Human β-factor XIIa which also Recognizes α-factor XIIa but not Factor XII or Complexes of Factor XIIa with C1 Esterase Inhibitor" *Thromb Haemost*, 83:874-881.

European Patent Application No. 11157555.1: Extended European Search Report, dated Jan. 26, 2012; 18 pages.

European Patent Application No. 11157555.1: Partial European Search Report, dated Sep. 22, 2011; 10 pages.

European Patent Application No. 11157557.7: Extended Search Report and Opinion, dated Sep. 19, 2011; 11 pages.

European Patent Application No. 11175105.3: Extended Search Report and Opinion, dated Jan. 12, 2012; 8 pages.

European Patent Application No. 12153341.8: Extended Search Report and Opinion, dated Aug. 7, 2012; 8 pages.

Francis, G.E. (May 1992) "Protein Modifications and Fusion Proteins" *Focus on Growth Factors*, 3(2):1-10.

Frantz, et al., 2007. "Targeting coagulation factor XII to protect from cardiac ischemia reperfusion injury," *Circulation* 116:II_134; Abstract 714.

Frohman, E.M. et al. (2006) "Multiple Sclerosis—The Plaque and Its Pathogenesis" *N Engl J Med*, 354:942-955.

Gancz, D. et al. (2009) "Involvement of the c-jun N-terminal kinases JNK1 and JNK2 in complement-mediated cell death" *Molecular Immunology*, 47:310-317.

Gesuete, R. et al. (2009) "Recombinant C1 Inhibitor in Brain Ischemic Injury" *Annals of Neurology*, 66(3):332-342.

Giles, A.R. et al. (1980) "The Thrombogenicity of Prothrombin Complex Concentrates: 1. The Relationship Between In Vitro Characteristics and In Vivo Thrombogenicity in Rabbits" *Thrombosis Research*, 17:353-366.

Girolami, A. et al. (2004) "The Occasional Venous Thromboses Seen in Patients With Severe (Homozygous) FXII Deficiency Are Probably Due to Associated Risk Factors: A Study of Prevalence in 21 Patients and Review of the Literature" *J Thrombosis Thrombolysis*, 17(2):139-143.

Göbel, K. et al. (2011) "Blockade of the Kinin Receptor B1 Protects from Autoimmune CNS Disease by Reducing Leukocyte Trafficking" *J Autoimmunity*, 36:106-114.

Graham, K.L. et al. (Nov. 15, 2009) "Chemokine-Like Receptor-1 Expression by Central Nervous System-Infiltrating Leukocytes and Involvement in a Model of Autoimmune Demyelinating Disease" *J Immunol*, 183(10):6717-6723. NIH Public Access Author Manuscript; available in PMC Jul. 14, 2010; 21 pages.

Gruenwald, C. et al. (2010) "Management and Monitoring of Anticoagulation for Children Undergoing Cardiopulmonary Bypass in Cardiac Surgery" *J Extra Corp Technol*, 42:9-19.

Grünenfelder, et a., Increased Susceptibility of the Left Compared to the Right Ventricle to Remote Ischemia/Reperfusion Injury in

(56) References Cited

OTHER PUBLICATIONS

Human C1-Inhibitor-Overexpression Transgene Mice, *Journal of Investigative Surgery*, 2002: 281-286.
Hack, C. E., et al., Safety of C1-inhibitor for Clinical Use, *Circulation* 2002; 106(18): e132.
Hagedorn et al, 2010, "Factor XIIa inhibitor recombinant human albumin Infestin-4 abolishes occlusive arterial thrombus formation with affecting bleeding," *Circulation* 121(13):1510-1517.
Hagedorn, I. et al. (2010) "In Vivo Antithrombotic Effect of a Novel Coagulation Factor XIIa Inhibitor in Murine Arterial Thrombosis and Stroke" *Hämostaseologie*, 30(1): A98, Abstract p. 15-11.
Hajishengallis, G. and J.D. Lambris (2010) "Crosstalk pathways between Toll-like receptors and the complement system" *Trends Immunol*, 31:154-163.
Halbmayer, W.-M. et al. (1993) "Faktor-XII-(Hageman-Faktor-) Mangel: ein Risikofaktor für die Entstehung von Thromboembolien (Factor XII (Hageman Factor) Deficiency: A Risk Factor in the Development of Thromboembolism)" *Wiener Medizinische Wochenschrift*, 143:43-50. English Summary, p. 43.
Han, E.D. et al. (Apr. 2002) "Increased vascular permeability in C1 inhibitor—deficient mice mediated by the bradykinin type 2 receptor" *J Clin Invest*, 109:1057-1063.
Hart, R. and D.R. Greaves (2010) "Chemerin Contributes to Inflammation by Promoting Macrophage Adhesion to VCAM-1 and Fibronectin through Clustering of VLA-4 and VLA-5" *J Immunol*, 185:3728-3739.
Heijnen et al., "Inhibition of classical complement activation attenuates liver ischemia and reperfusion injury in a rat model," *Clinical and Experimental Immunology*, 2005, pp. 15-23 (Year: 2005).
Heimann, A. et al. (1999) "C1-esterase inhibitor reduces infarct volume after cortical vein occlusion" *Brain Research*, 838(1-2):210-213.
Heller, et al., "The Complement Regulators C1 Inhibitor and Soluble Complement Receptor 1 Attenuate Acute Lung Injury in Rabbits," *Shock*, 2000; 285-290.
Heller, et al., "Selection of a C5a Receptor Antagonist from Phage Libraries Attenuating the Inflammatory Response in Immune Complex Disease and Ischemia/Reperfusion Injury," *J Immunol* 1999; 163:985-994.
Herrmann, A.M. et al. (2010) "Glatiramer Acetate Attenuates Pro-Inflammatory T Cell Responses but Does Not Directly Protect Neurons from Inflammatory Cell Death" *Am J Pathol*, 177(6):3051-3060.
Hezareh, M. et al. (2001) "Effector Function Activities of a Panel of Mutants of a Broadly Neutralizing Antibody against Human Immunodeficiency Virus Type 1" *J Virol*, 75(24):12161-12168.
Hill, et al., "Soluble Complement Receptor Type 1 Ameliorates the Local and Remote Organ Injury After Intestinal and Ischemia-Reperfusion in the Rat," *The Journal of Immunology*, 1992; pp. 1723-1728.
Horstick. 2002. "C1-Esterase Inhibitor in Ischemia and Reperfusion," *Immunobiology*, 205(4-5): 552-562.
Horstick, G. et al., "Application of C1-Esterase Inhibitor During Reperfusion of Ischemic Myocardium: Dose-Related Beneficial Versus Detrimental Effects," *Circulation*, 2001: 104(25): 3125-3131.
International Search Report and Written Opinion issued in International Patent Application No. PCT/EP2012/054142, dated Jul. 27, 2012; 20 pages.
International Search Report and Written Opinion issued in International Patent Application No. PCT/EP2012/054149, dated Apr. 18, 2012; 12 pages.
International Search Report and Written Opinion issued in International Patent Application No. PCT/EP2012/064322, dated Aug. 28, 2012; 15 pages.
International Search Report and Written Opinion issued in International Patent Application No. PCT/EP2012/068643, dated Jun. 12, 2012; 16 pages.
International Search Report and Written Opinion issued in International Patent Application No. PCT/EP2013/051832, dated Apr. 3, 2013; 14 pages.
Ihrcke, et al. 1998. "Regulation of platelet heparanase during inflammation: role of pH and proteinases," *J Cell Physiol* 175(3): 255-267.
Ihrcke, N. S., and J. L. Platt. 1996. "Shedding of heparan sulfate proteoglycan by stimulated endothelial cells: evidence for proteolysis of cell-surface molecules," *J Cell Physiol* 168(3): 625-637.
Inderbitzin, et al., 2004. "Local and remote ischemia-reperfusion injury is mitigated in mice overexpressing human C1 inhibitor," *Eur Surg Res* 36: 142-147.
International Search Report issued in International Patent Application No. PCT/EP2014/054489, dated Apr. 10, 2014 (5 pages).
International Search Report and Written Opinion issued in International Patent Application No. PCT/EP2014/063691, dated Sep. 25, 2014; 17 pages.
Isawa et al. 2002 "A mosquito salivary protein inhibits activation of the plasma contact system by binding to Factor XII and high molecular weight kininogen," *J. Biol. Chem*. 277:27651-27658.
Japanese Patent Application No. 2013-557120: English translation of Office Action, dated Dec. 1, 2015, 3 pages.
Johnson, et al., 2002. "Receptor-mediated monitoring of tissue well-being via detection of soluble heparan sulfate by Toll-like receptor 4," *J Immunol* 168.
Jostock, T. et al. (2004) "Rapid generation of functional human IgG antibodies derived from Fab-on-phage display libraries" *J Immunol Methods*, 289:65-80.
Jung, K-H. et al. (2009) "Augmentation of nitrite therapy in cerebral ischemia by NMDA receptor inhibition" *Biochem Biophys Res Commun*, 378:507-512.
Kalogeris, et al., "Cell Biology of Ischemia/Reperfusion Injury," *Int Rev Cell Mol Biol.*, 2012, p. 229-317 (2012).
Kannemeier, C. et al. (Apr. 10, 2007) "Extracellular RNA constitutes a natural procoagulant cofactor in blood coagulation" *PNAS*, 401(15):6388-6393.
Kassimatis, T. et al., "A double-blind randomized controlled investigation into the efficacy of Microcept (APT070) for preventing ischaemia reperfusion injury in the kidney allograft (EMPIRIKAL): study protocol for a randomized controlled trial," *Trials*, 2017: 18:255 (11 pages).
Katseni, et al., "The Effect of Perioperative Ischemia and Reperfusion on Multiorgan Dysfunction following Abdominal Aortic Aneurysm Repair," *BioMed Research International*, 2015, pp. 1-11.
Kleinschnitz et al., 2006, "Targeting coagulation factor XII provides protection from pathological thrombosis in cerebral ischemia without interfering with hemostasis," *J Exp Med*. 203(3):513-518.
Knipp et al. (2005) "Small ischemic brain lesions after cardiac valve replacement detected by diffusion-weighted magnetic resonance imaging: relation to neurocognitive function" *Eur J Cardio-thorac Surg*, 28:88-96.
Kobayashi, S. et al. (Oct. 1997) "Subcortical Silent Brain Infarction as a Risk Factor for Clinical Stroke" *Stroke*, 28(10):1932-1939.
Köhler, G. and C. Milstein (1975) "Continuous cultures of fused cells secreting antibody of predefined specificity" *Nature*, 256:495-497.
Koo, C. B. et al., "Tetracycline-dependent expression of the human erythropoietin gene in transgenic chickens," *Transgenic Res*, 2010; 19:437-447.
Koster, T. et al. (1994) "John Hageman's factor and deep-vein thrombosis: Leiden Thrombophilia Study" *Br J Haematol*, 87:422-424.
Koster, A. et al. (2010) "Anticoagulation in Cardiac Surgery" Chapter 43 in *Hämostaseologie*, 2nd Edition. B. Pötzch and K. Madlener (Eds.) Germany: Springer-Verlag, pp. 638-645; with machine translation.
Koster, A. et al. (Feb. 1, 2004) "Effectiveness of Bivalirudin as a Replacement for Heparin During Cardiopulmonary Bypass in Patients Undergoing Coronary Artery Bypass Grafting" *Am J Cardiol*, 93:356-359.
Kozbor, D. and J.C. Roder (1983) "The production of monoclonal antibodies from human lymphocytes" *Immunology Today*, 4:72-79.

(56) References Cited

OTHER PUBLICATIONS

Krishnamoorthy, G. and H. Wekerle (2009) "Autoimmune Disease: Multiple Sclerosis" *Eur J Immunol*, 39:2031-2035.
Kuhli, C. et al. (2004) "Factor XII Deficiency: A Thrombophilic Risk Factor for Retinal Vein Occlusion" *Am J Ophthalmol*, 137:459-464.
Kuijpers, M.J.E. et al. (2014) "Factor XII Regulates the Pathological Process of Thrombus Formation on Ruptured Plaques" *Arterioscler Thromb Vasc Biol*, 1674-1680.
Kunkel, T.A. et al. (1987) "Rapid and Efficient Site-Specific Mutagenesis without Phenotypic Selection" *Methods Enzymol*, 154:367-382.
Kurtzke, J.F. (2008) "Historical and Clinical Perspectives of the Expanded Disability Status Scale" *Neuroepidemiology*, 31:1-9.
Langrish, C.L. et al. (2005) "IL-23 Drives a Pathogenic T Cell Population That Induces Autoimmune Inflammation" *J Exp Med*, 201:233-240.
Lapchak, P. H. et al., "Inhibition of Syk activity by R788 in platelets prevents remote lung tissue damage after mesenteric ischemia-reperfusion injury," *Am J Physiol Gastrointest Liver Physiol*, 2012; 302: G1416-G1422.
Larsson, M. et al. (2014) "A Factor XIIa Inhibitory Antibody Provides Thromboprotection in Extracorporeal Circulation Without Increasing Bleeding Risk" *Sci Transl Med*, 6:222ra17; 14 pages.
Laskowski and Kato, 1980. "Protein inhibitors of proteinases,"*Annu. Rev. Biochem.* 49:593-626.
Lee, D.-H. et al. (2010) "Compounds Acting on the Renin-Angiotensin-Aldosterone System as Potential Regulators of Autoimmune Neuroinflammation" *Drugs of the Future*, 35(5):393-398.
Lichenstein, H. et al. (Jul. 8, 1994) "Afamin Is a New Member of the Albumin, α-Fetoprotein, and Vitamin D-binding Protein Gene Family" *J Biol Chem*, 269(27):18149-18154.
Liistro, F. and C. Di Mario (2003) "Carotid Artery Stenting" *Heart*, 89:944-948.
Liu, D., et al. 2007. "C1 inhibitor-mediated protection from sepsis," *J Immunol* 179: 3966-3972.
Lloyd-Jones et al. (2009) "Heart Disease and Stroke Statistics—2009 Update: A Report from the American Heart Association Statistics Committee and Stroke Statistics Subcommittee" *Circulation*, 119:e21-e181.
Longa, E.Z. et al. (1989) "Reversible middle cerebral artery occlusion without craniectomy in rats" *Stroke*, 20:84-91.
Longhi, L. et al. (2009) "C1-inhibitor attenuates neurobehavioral deficits and reduces contusion volume after controlled cortical impact brain injury in mice" *Crit. Care Med.*, 37(2):659-665.
Lopez, O.L. et al. (Oct. 2003) "Risk Factors for Mild Cognitive Impairment in the Cardiovascular Health Study Cognition Study" *Arch. Neurol.*, 60:1394-1399.
Lu, F. et al., (2008) "The effect of C1 inhibitor on intestinal ischemia and reperfusion injury," *Am J Phyisol Gastrointest Liver Physiol*, 195: G1042-G1049.
Lu, F. et al., 2008 "The effect of C1 inhibitor on intestinal ischaemia and reperfusion injury", *Molecular Immunology* 45(16):4156.
Ma, J. et al. (2001) "Synergistic protective effect of caspase inhibitors and bFGF against brain injury induced by transient focal ischaemia" *Br J Pharmacol*, 133:345-350.
Mackman, N. (2004) "Role of tissue factor in hemostasis, thrombosis, and vascular development" *Arterioscler Thromb Vasc Biol*, 24:1015-1022.
Malik, F. et al. (1992) "Polyethylene Glycol (PEG)-modified Granulocyte-Macrophage Colony-stimulating Factor (GM-CSF) with Conserved Biological Activity" *Exp Hematol*, 20:1028-1035.
Marik, C. et al. (Nov. 2007) "Lesion Genesis in a Subset of Patients With Multiple Sclerosis: A Role for Innate Immunity?" *Brain*, 130:2800-2815. Europe PMC Funders Group, Author Manuscript; available in PMC Nov. 16, 2010; 26 pages.
Mathison, S. et al. (1998) "Nasal Route for Direct Delivery of Solutes to the Central Nervous System: Fact or Fiction?" *J Drug Target*, 5:415-441.
Morales, Y. et al. (2006) "The Pathology of Multiple Sclerosis: Evidence for Heterogeneity" *Adv Neurol*, 98:27-45.
Moskowitz, D.M. et al. (2006) "Use of the Hemobag® for Modified Ultrafiltration in a Jehovah's Witness Patient Undergoing Cardiac Surgery" *JECT*, 38:265-270.
Müller, F. et al. (Dec. 11, 2009) "Platelet Polyphosphates Are Proinflammatory and Procoagulant Mediators In Vivo" *Cell*, 139(6):1143-1156. NIH Public Access Author Manuscript; available in PMC Dec. 11, 2010; 22 pages.
Murakami, K. et al. (Jan. 1, 1998) "Mitochondrial Susceptibility to Oxidative Stress Exacerbates Cerebral Infarction That Follows Permanent Focal Cerebral Ischemia in Mutant Mice with Manganese Superoxide Dismutase Deficiency" *J Neurosci*, 18:205-213.
Nahrendorf, M. et al. (Feb. 11, 2008) "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury" *Circulation*, 117:1153-1160.
Nahrendorf, M. et al. (Feb. 27, 2006) "Factor XIII Deficiency Causes Cardiac Rupture, Impairs Wound Healing, and Aggravates Cardiac Remodeling in Mice With Myocardial Infarction" *Circulation*, 113:1196-1202.
National Institute of Neurological Disorders and Stroke, "Multiple Sclerosis: Hope Through Research" [online]. http://www.ninds.nih.gov/disorders/multiple_sclerosis/detail_multiple_sclerosis.htm?css=print; pp. 1-19; accessed Sep. 7, 2016.
National Institute of Neurological Disorders and Stroke, "Neuromyelitis Optica Information Page" [online]. http://www.ninds.nih.gov/disorders/neuromyelitis_optica/neuromyelitis_optica.htm; accessed Sep. 7, 2016; pp. 1-4.
National Institute of Neurological Disorders and Stroke, "Transverse Myelitis Fact Sheet" [online]. http://www.ninds.nih.gov/disorders/transversemyelitis/detail_transversemyelitis.htm?css=print; pp. 1-9; accessed Sep. 7, 2016.
Needleman, S.B. and C.D. Wunsch (1970) "A General Method Applicable to the Search for Similarities in the Amino Acid Sequence of Two Proteins" *J. Mol. Biol.*, 48:443-453.
Neher, et al., "Molecular mechanism of inflammation and tissue injury after major trauma—is complement the "bad guy"?", *Journal of Biomedical Science*, 2011, 1-6.
New Zealand Patent Application No. 619385: First Examination Report, dated Nov. 24, 2014; 2 pages.
Newman, M. et al. (Feb. 8, 2001) "Longitudinal Assessment of Neurocognitive Function After Coronary-artery Bypass Surgery" *NEJM*, 344(6):395-402.
Nielsen, et al. 2002. "C1-inhibitor reduces the ischaemia-reperfusion injury of skeletal muscles in mice after aortic cross-clamping," *Scand J Immunol* 56: 588-592.
Nielsen, W. E. et al., "Effect of supraphysiologic levels of C1-inhibitor on the classical, lectin and alternative pathways of complement," *Molecular Immunology*, 2007; 44: 1819-1826.
Noseworthy et al. (2000) "Multiple Sclerosis" *N Engl J Med*, 343(13):938-952.
Nuijens et al., 1989, "Activation of the contact system of coagulation by a monoclonal antibody directed against a neodeterminant in the heavy chain region of human coagulation factor XII," *J. Biol. Chem.* 264(22):12941-49.
Okun, E. et al. (May 2011) "Toll-like receptor signaling in neural plasticity and disease" *Trends Neurosci.*, 34(5):269-281.
Okuno, S. et al. (2004) "The c-Jun N-Terminal Protein Kinase Signaling Pathway Mediates Bax Activation and Subsequent Neuronal Apoptosis through Interaction with Bim after Transient Focal Cerebral Ischemia" *J Neurosci*, 24(36):7879-7887.
Osanai, T. and Y. Nagai (1984) "Suppression of Experimental Allergic Encephalomyelitis with Liposome-Encapsulated Protease Inhibitor Therapy Through the Blood-Brain Barrier" *Neurochemical Research*, 9(10):1407-1416 (abstract only).
Oschatz, C. et al. (Feb. 25, 2011) "Mast Cells Increase Vascular Permeability by Heparin-Initiated Bradykinin Formation In Vivo" *Immunity*, 34:258-268.
Osthoff, M. et al. (2011) "Mannose-Binding Lectin Deficiency Is Associated With Smaller Infarction Size and Favorable Outcome in Ischemic Stroke Patients" *PLoS One*, 6(6):e21338; 8 pages.

(56) References Cited

OTHER PUBLICATIONS

Pearson, W.R. and D.J. Lipman (Apr. 1988) "Improved tools for biological sequence comparison" *Proc. Natl. Acad. Sci. USA*, 85:2444-2448.
Pixley et al. 1987, "A monoclonal antibody recognizing an icosapeptide sequence in the heavy chain of human factor XII inhibits surface-catalyzed activation," *J Biol Chem* 262(21):10140-45.
Platt, et al., 1990. "Release of heparan sulfate from endothelial cells. Implications for pathogenesis of hyperacute rejection," *J Exp Med* 171(4): 1363-1368.
Polman, C.H. et al. "Diagnostic Criteria for Multiple Sclerosis: 2010 Revisions to the McDonald Criteria" *Ann Neurol*, 69:292-302.
Pysz, M.A. et al. (2000) "Molecular imaging: current status and emerging strategies" *Clinical Radiology*, 65:500-516.
Qu, Z. and E.L. Chaikof (Oct. 2010) "Interface Between Hemostasis and Adaptive Immunity" Curr Opin Immunol, 22(5):634-642. NIH Public Access Author Manuscript; available in PMC Aug. 27, 2012; 13 pages.
Querol, M. et al. (Apr. 12, 2006) "A paramagnetic contrast agent with myeloperoxidase-sensing properties" *Organic and Biomolecular Chemistry*, 4:1887-1895.
Ragonese, P. et al. (2008) "Mortality in Multiple Sclerosis: A Review" *Eur J Neurol*, 15:123-127.
Ratnoff, O.D. et al. (Apr. 1955) "A Familial Hemorrhagic Trait Associated With a Deficiency of a Clot-Promoting Fraction of Plasma" *J Clin Invest*, 34:602-613.
Ravon et al., 1995. "Monoclonal antibody F1 binds to the kringle domain of factor XII and induces enhanced susceptibility for cleavage by kallikrein," *Blood* 86(11):4134-43.
Renné, T. et al. (Jul. 18, 2005) "Defective thrombus formation in mice lacking factor XII" *J Exp Med*, 202(2):271-281.
Rodriguez, E. et al. (Jan. 13, 2010) "Activatable magnetic resonance imaging agents for myeloperoxidase sensing: mechanism of activation, stability and toxicity" *J Am Chem Soc*, 132(1):168-177. NIH Public Access Author Manuscript; available in PMC Jan. 13, 2010; 21 pages.
Ronald, J.A. et al. (Aug. 3, 2009) "Enzyme-Sensitive Magnetic Resonance Imaging Targeting Myeloperoxidase Identifies Active Inflammation in Experimental Rabbit Atherosclerotic Plaques" *Circulation*, 120:592-599.
Rosenkranz, M. et al. (Jan. 2006) "The Amount of Solid Cerebral Microemboli during Cartoid Stenting Does Not Relate to the Frequency of Silent Ischemic Lesions" *Am J Neuroradiol*, 27:157-161.
Sakai, N. et al. (1991) "Thromboembolic Risks During Cerebral Angiography With Low Osmolar Contrast Media—Ionic Versus Non-Ionic Contrast Media" *The Clinical Report*, 25(9):153-157, with partial English translation.
Sander, G.E. and T.D. Giles (2004) "Ximelagatran: Light at the end of the tunnel or the next tunnel?" *Am J Geriatr Cardiol*, 13(4); 4 pages.
Sato, Y. et al. (2009) "White Matter Activated Glial Cells Produce BDNF in a Stroke Model of Monkeys" *Neuroscience Research*, 65:71-78.
Scheinfeld, N.S. et al. (Feb. 3, 2016) "Intravenous Immunoglobulin" [online]. *Medscape. Reference. Drugs, Diseases & Procedures.* WebMD, LLC: http://emedicine.medscape.com/article/210367-overview, 13 pages. Retrieved on Jun. 8, 2016.
Schmaier, A.H. and G. Larusch (2010) "Factor XII: New life for an old protein" *Thromb Haemost*, 104:915-918.
Schmaier, A.H. (2008) "Assembly, Activation, and Physiologic Influence of the Plasma Kallikrein/Kinin System" *Int Immunopharmacol.*, 8:161-165.
Schmaier, A. (Sep. 2008) "The elusive physiologic role of Factor XII" *J Clin Invest*, 118(9):3006-3009.
Schmaier, A.H. (Feb. 5, 2014) "Extracorporeal Circulation Without Bleeding" *Science Translational Medicine*, 6(222):222fs7; 3 pages.
Schuhmann, M.K. et al. (2010) "Stromal Interaction Molecules 1 and 2 Are Key Regulators of Autoreactive T Cell Activation in Murine Autoimmune Central Nervous System Inflammation" *J Immunol*, 184:1536-1542.
Shields, R.L. et al. (2001) "High Resolution Mapping of the Binding Site on Human IgG1 for FcγRI, FcγRII, FcγRIII, and FcRn and Design of IgG1 Variants with Improved Binding to the FcγR" *J Biol Chem*, 276(9):6591-6604.
Sidhu, S.S. et al. (2000) "Phage Display for Selection of Novel Binding Peptides" *Methods Enzymol*, 328:333-363.
Small et al., 1985. "A monoclonal antibody that inhibits activation of human Hageman factor (factor XII)," *Blood* 65(1):202-10.
Smith, T.F. and M.S. Waterman (1981) "Comparison of Biosequences" *Advances Applied Mathematics*, 2:482-489.
Sobel, R.A. and M.E. Mitchell (1989) "Fibronectin in Multiple Sclerosis Lesions" *Am J Pathol*, 135:161-168.
Souza, et al., 2004. "Role of bradykinin B2 and B1 receptors in the local, remote, and systemic inflammatory responses that follow intestinal ischemia and reperfusion injury," *J Immunol* 172: 2542-2548.
Sperling, C. et al. (2009) "Blood coagulation on biomaterials requires the combination of distinct activation processes" *Biomaterials*, 30:4447-4456.
Stavrou, E. and A.H. Schmaier (2010) "Factor XII: What Does It Contribute to Our Understanding of the Physiology and Pathophysiology of Hemostasis & Thrombosis" *Thromb Res*, 125:210-215.
Stieh, J. et al. (1996) "Capillary Leak Syndrome after Open Heart Surgery for Congenital Heart Defects: Therapy with C1-Inhibitor" *Biomed Prog*, 9:13-16.
Storini, et al., 2005. "C1-inhibitor protects against brain ischemia-reperfusion injury via inhibition of cell recruitment and inflammation," *Neurobiol. Dis* 19: 10-17.
Strom, T.B. and M. Suthanthiran, "Therapeutic Approach to Organ Transplantation" in *Therapeutic Immunology*. K. Frank Austen et al. (eds.), Cambridge, Massachusetts: Blackwell Science, 1996; pp. 451-456.
Stutz, B. (Jan. 9, 2009) "Pumphead: Does the heart-lung machine have a dark side?" Scientific American, [online]. Retrieved from: http://www.scientificamerican.com/article/pumphead-heart-lung-machine, on Sep. 23, 2014; 8 pages.
Stüve, O. et al. (2010) "Translational Research in Neurology and Neuroscience 2010" *Arch Neurol*, 67:1307-1315.
Szeplaki, G. et al. (2009) "Strong complement activation after acute ischemic stroke is associated with unfavorable outcomes" *Atherosclerosis*, 204:315-320.
Tans et al., 1987, "Studies on the effect of serine protease inhibitors on activated contact factors. Application in amidolytic assays for factor XIIa, plasma kallikrein and factor Xia," *Eur. J. Biochem.* 164(3):637-42.
The International Multiple Sclerosis Genetics Consortium & The Wellcome Trust Case Control Consortium 2 (2011) "Genetic Risk and a Primary Role for Cell-Mediated Immune Mechanisms in Multiple Sclerosis" *Nature*, 476:214-219.
Toomayan, et al., 2003. "C1-esterase inhibitor and a novel peptide inhibitor improve contractile function in reperfused skeletal muscle," *Microsurgery* 23: 561-567.
Tung, C-H. et al. (2003) "Novel Factor XIII Probes for Blood Coagulation Imaging" *ChemBioChem*, 4:897-899.
U.S. Appl. No. 61/510,801, filed Jul. 2, 2011, by Panousis et al.
Vermeer, S.E. et al. (Apr. 10, 2003) "Silent Brain Infarcts and White Matter Lesions Increase Stroke Risk in the General Population: The Rotterdam Scan Study" *Stroke*, 34:1126-1129.
Vinci, G. et al., "In Vivo Biosynthesis of Endogenous and of Human C1 Inhibitor in Transgenic Mice: Tissue Distribution and Colocalization of Their Expression," *J Immunology*, 2002; 169:5948-5954.
Wachtfogel, Y.T. et al. (1986) "Purified Plasma Factor XIIa Aggregates Human Neutrophils and Causes Degranulation" *Blood*, 67:1731-1737.
Wang, Y. et al. (2008) "Gene inactivation of Na+/H+ exchanger isoform 1 attenuates apoptosis and mitochondrial damage following transient focal cerebral ischemia" *Eur J Neurosci*, 28(1):51-61.

(56) References Cited

OTHER PUBLICATIONS

Warren, B.L. et al. (Oct. 17, 2001) "High-Dose Antithrombin III in Severe Sepsis. A Randomized Controlled Trial" *JAMA*, 286:1869-1878.
Wen, L. et al. (1992) "Nucleotide sequence of a cDNA clone that encodes the maize inhibitor of trypsin and activated Hageman factor" *Plant Molecular Biology*, 18:813-814.
Wendel, H.P. et al. (1996) "Heparin-coated devices and high-does aprotinin optimally inhibit contact system activation in an in vitro cardiopulmonary bypass model" *Immunopharmacology*, 32:128-130.
Wendel, H.P. et al. (1996) "Influence of heparin, heparin plus aprotinin and hirudin on contact activation in a cardiopulmonary bypass model" *Immunopharmacology*, 32:57-61.
Werle, M. et al. (2006) "Strategies to improve plasma half life time of peptide and protein drugs" *Amino Acids*, 30:351-367.
Wessler, S. et al. (1955) "Studies in Intravascular Coagulation. III. The Pathogenesis of Serum-Induced Venous Thrombosis" *J Clin Invest*, 34(4):647-651.
Who 1$^{st}$ International Standard for C1-inhibitior, plasma, NIBSC code 08/262; Instructions for use, Version 2.0, Dated Oct. 27, 2010.
WHO International Standard WHO 1$^{st}$ International Standard for C1-inhibitor, plasma NIBSC code: 08/262, 2010—pp. 1-2.
Williams and Baird. 2003 "DX-88 and HAE: a developmental perspective," *Transfus Apheresis Sci.* 29(3): 255-258.
Woodruff, T. et al. (2011) "Pathophysiology, treatment, and animal and cellular models of human ischemic stroke" *Mol. Neurodegen.*, 6:11; 19 pages.
Yamagami, H. and Nobuyuki Sakai (2009) "Antiplatelet Therapy in Carotid Artery Stenting" *Japanese Journal of Thrombosis and Hemostasis* 20(6): 602-607, with partial English translation.
Yednock, T.A. et al. (1992) "Prevention of Experimental Autoimmune Encephalomyelitis by Antibodies Against α4β1 Integrin" *Nature*, 356:63-66.
Yu, J. et al. (1994) "Polymeric biomaterials: influence of phosphorylcholine polar groups on protein adsorption and complement activation" *Int J Artif Organs*, 17(9):499-504.
Zalevsky, J. et al. (Feb. 2010) "Enhanced antibody half-life improves in vivo activity" *Nature Biotech*, 28(2):157-159.
Zeerleder, S. et al. (1999) "Reevaluation of the Incidence of Thromboembolic Complications in Congenital Factor XII Deficiency" *Thromb Haemost*, 82:1240-1246.
Zeerleder, S. 2011. "C1-inhibitor: more than a serine protease inhibitor," *Semin Thromb Hemost*. 37: 362-374.
Zuraw, et al., "Phase II study results of a replacement therapy for hereditary angioedema with subcutaneous C1-inhibitor concentrate," *European Journal of Allergy*, 2015, 1319-1328.
U.S. Appl. No. 14/773,020, Restriction Requirement dated May 5, 2016, (7 pages).
U.S. Appl. No. 14/773,020, Nonfinal Rejection dated Oct. 3, 2016, (28 pages).
U.S. Appl. No. 14/773,020, Final Rejection dated Aug. 22, 2017, (24 pages).
U.S. Appl. No. 14/773,020, Nonfinal Rejection dated Apr. 5, 2018, (33 pages).
U.S. Appl. No. 14/773,020, Notice of Allowance dated Dec. 26, 2018, (7 pages).
U.S. Appl. No. 14/773,020, Corrected Notice of Allowability dated Jan. 14, 2019, (5 pages).
Van Veen, H.A. et al., "Characterization of recombinant human C1 inhibitor secreted in milk of transgenic rabbits," *Journal of Biotechnology*, 2012; 162: 319-326.
Blaisdell, "The pathophysiology of skeletal muscle ischemia and the reperfusion syndrome: a review," *Cardiovasc Surg.*, 2002, 10:620-630.
Bouillet, "Icatibant in hereditary angioedema: news and challenges," *Expert Rev Clin Immunol*, 2011, 7: 267-272.
Caliezi et al., "C1-Esterase inhibitor: an anti-inflammatory agent and its potential use in the treatment of diseases other than hereditary angioedema," *Pharmacol Rev.*, 2000, 52: 91-112.
Campos et al., "Identification and characterization of a novel factor XIIa inhibitor in the hematophagous insect, *Triatoma infestans* (Hemiptera: Reduviidae), " *FEBS Lett.*, 2004, 577(3):512-516.
Jaisser, "Inducible Gene Expression and Gene Modification in Transgenic Mice," *J Am Soc Nephrol*, 2000, 11:S95-S100.
Tang et al., "Pivotal role for neuronal Toll-like receptors in ischemic brain injury and functional deficits," *PNAS*, 2007, 104(34):13798-13803.
Tatusova et al., "BLAST 2 Sequences, a new tool for comparing protein and nucleotide sequences," *FEMS Microbiol. Lett.*, 1999, 174(2):247-250.
Menache et al., "Antithrombin III: physiology, deficiency, and replacement therapy," *Transfusion*, 1992, 32(6):580-588.

\* cited by examiner

SEQUENCE LISTING

<160> NUMBER OF SEQ ID NOS: 19

<210> SEQ ID NO 1
<211> LENGTH: 478
<212> TYPE: PRT
<213> ORGANISM: Homo sapiens

<400> SEQUENCE: 1

```
Asn Pro Asn Ala Thr Ser Ser Ser Gln Asp Pro Glu Ser Leu Gln
1               5                   10                  15

Asp Arg Gly Glu Gly Lys Val Ala Thr Thr Val Ile Ser Lys Met Leu
                20                  25                  30

Phe Val Glu Pro Ile Leu Glu Val Ser Ser Leu Pro Thr Thr Asn Ser
            35                  40                  45

Thr Thr Asn Ser Ala Thr Lys Ile Thr Ala Asn Thr Thr Asp Glu Pro
        50                  55                  60

Thr Thr Gln Pro Thr Thr Glu Pro Thr Thr Gln Pro Thr Ile Gln Pro
65                  70                  75                  80

Thr Gln Pro Thr Thr Gln Leu Pro Thr Asp Ser Pro Thr Gln Pro Thr
                85                  90                  95

Thr Gly Ser Phe Cys Pro Gly Pro Val Thr Leu Cys Ser Asp Leu Glu
            100                 105                 110

Ser His Ser Thr Glu Ala Val Leu Gly Asp Ala Leu Val Asp Phe Ser
        115                 120                 125

Leu Lys Leu Tyr His Ala Phe Ser Ala Met Lys Lys Val Glu Thr Asn
    130                 135                 140
```

```
Met Ala Phe Ser Pro Phe Ser Ile Ala Ser Leu Leu Thr Gln Val Leu
145                 150                 155                 160

Leu Gly Ala Gly Glu Asn Thr Lys Thr Asn Leu Glu Ser Ile Leu Ser
            165                 170                 175

Tyr Pro Lys Asp Phe Thr Cys Val His Gln Ala Leu Lys Gly Phe Thr
        180                 185                 190

Thr Lys Gly Val Thr Ser Val Ser Gln Ile Phe His Ser Pro Asp Leu
    195                 200                 205

Ala Ile Arg Asp Thr Phe Val Asn Ala Ser Arg Thr Leu Tyr Ser Ser
210                 215                 220

Ser Pro Arg Val Leu Ser Asn Asn Ser Asp Ala Asn Leu Glu Leu Ile
225                 230                 235                 240

Asn Thr Trp Val Ala Lys Asn Thr Asn Lys Ile Ser Arg Leu Leu
                245                 250                 255

Asp Ser Leu Pro Ser Asp Thr Arg Leu Val Leu Leu Asn Ala Ile Tyr
            260                 265                 270

Leu Ser Ala Lys Trp Lys Thr Thr Phe Asp Pro Lys Lys Thr Arg Met
    275                 280                 285

Glu Pro Phe His Phe Lys Asn Ser Val Ile Lys Val Pro Met Met Asn
290                 295                 300

Ser Lys Lys Tyr Pro Val Ala His Phe Ile Asp Gln Thr Leu Lys Ala
305                 310                 315                 320

Lys Val Gly Gln Leu Gln Leu Ser His Asn Leu Ser Leu Val Ile Leu
                325                 330                 335

Val Pro Gln Asn Leu Lys His Arg Leu Glu Asp Met Glu Gln Ala Leu
            340                 345                 350

Ser Pro Ser Val Phe Lys Ala Ile Met Glu Lys Leu Glu Met Ser Lys
    355                 360                 365

Phe Gln Pro Thr Leu Leu Thr Leu Pro Arg Ile Lys Val Thr Thr Ser
    370                 375                 380

Gln Asp Met Leu Ser Ile Met Glu Lys Leu Glu Phe Phe Asp Phe Ser
385                 390                 395                 400

Tyr Asp Leu Asn Leu Cys Gly Leu Thr Glu Asp Pro Asp Leu Gln Val
                405                 410                 415

Ser Ala Met Gln His Gln Thr Val Leu Glu Leu Thr Glu Thr Gly Val
            420                 425                 430

Glu Ala Ala Ala Ser Ala Ile Ser Val Ala Arg Thr Leu Leu Val
    435                 440                 445

Phe Glu Val Gln Gln Pro Phe Leu Phe Val Leu Trp Asp Gln Gln His
450                 455                 460

Lys Phe Pro Val Phe Met Gly Arg Val Tyr Asp Pro Arg Ala
465                 470                 475

<210> SEQ ID NO 2
<211> LENGTH: 48
<212> TYPE: PRT
<213> ORGANISM: Triatoma infestans

<400> SEQUENCE: 2

Glu Val Arg Asn Pro Cys Ala Cys Phe Arg Asn Tyr Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45
```

<210> SEQ ID NO 3
<211> LENGTH: 56
<212> TYPE: PRT
<213> ORGANISM: Homo sapiens
<223> OTHER INFORMATION: SPINK-1

<400> SEQUENCE: 3

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 129
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Arg Pro Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser

<210> SEQ ID NO 8

```
<211> LENGTH: 110
<212> TYPE: PRT
<213> ORGANISM: Homo sapiens

<400> SEQUENCE: 8

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110

<210> SEQ ID NO 9
<211> LENGTH: 5
<212> TYPE: PRT
<213> ORGANISM: Homo sapiens

<400> SEQUENCE: 9

Lys Tyr Ile Met Gln
1               5

<210> SEQ ID NO 10
<211> LENGTH: 17
<212> TYPE: PRT
<213> ORGANISM: Homo sapiens

<400> SEQUENCE: 10

Gly Ile Arg Pro Ser Gly Gly Thr Thr Val Tyr Ala Asp Ser Val Lys
1               5                   10                  15

Gly

<210> SEQ ID NO 11
<211> LENGTH: 17
<212> TYPE: PRT
<213> ORGANISM: Artificial
<220> FEATURE:
<223> OTHER INFORMATION: Heavy chain CDR2 showing variations
<220> FEATURE:
<221> NAME/KEY: V-segment
<222> LOCATION: (3)..(3)
<223> OTHER INFORMATION: Xaa is selected from Arg, Asn, and Asp
<220> FEATURE:
<221> NAME/KEY: V-segment
<222> LOCATION: (4)..(4)
<223> OTHER INFORMATION: Xaa is selcted from Pro, Val, Ile and Met
<220> FEATURE:
<221> NAME/KEY: V-segment
<222> LOCATION: (5)..(5)
<223> OTHER INFORMATION: Xaa is selected from Ser, Pro and Ala
<220> FEATURE:
<221> NAME/KEY: V-segment
<222> LOCATION: (6)..(6)
<223> OTHER INFORMATION: Xaa is selected from Gly, Leu, Val and Thr
<220> FEATURE:
<221> NAME/KEY: V-segment
<222> LOCATION: (7)..(7)
<223> OTHER INFORMATION: Xaa is selected from Gly, Tyr, Gln, Lys, Arg,
    Asn and Met
```

```
<220> FEATURE:
<221> NAME/KEY: V-segment
<222> LOCATION: (8)..(8)
<223> OTHER INFORMATION: Xaa is selected from Thr, Gly and Ser

<400> SEQUENCE: 11

Gly Ile Xaa Xaa Xaa Xaa Xaa Thr Val Tyr Ala Asp Ser Val Lys
1               5                   10                  15

Gly

<210> SEQ ID NO 12
<211> LENGTH: 20
<212> TYPE: PRT
<213> ORGANISM: Homo sapiens

<400> SEQUENCE: 12

Ala Leu Pro Arg Ser Gly Tyr Leu Ile Ser Pro His Tyr Tyr Tyr
1               5                   10                  15

Ala Leu Asp Val
            20

<210> SEQ ID NO 13
<211> LENGTH: 20
<212> TYPE: PRT
<213> ORGANISM: Artificial
<220> FEATURE:
<223> OTHER INFORMATION: Heavy chain CDR3 showing variations
<220> FEATURE:
<221> NAME/KEY: V-segment
<222> LOCATION: (9)..(9)
<223> OTHER INFORMATION: Xaa is selected from Ile, Met and Val
<220> FEATURE:
<221> NAME/KEY: V-segment
<222> LOCATION: (10)..(10)
<223> OTHER INFORMATION: Xaa is selcted from Ser and Lys
<220> FEATURE:
<221> NAME/KEY: V-segment
<222> LOCATION: (11)..(11)
<223> OTHER INFORMATION: Xaa is selected from Pro, Lys, Thr and His
<220> FEATURE:
<221> NAME/KEY: V-segment
<222> LOCATION: (12)..(12)
<223> OTHER INFORMATION: Xaa is selected from His, Asn, Gly and Gln

<400> SEQUENCE: 13

Ala Leu Pro Arg Ser Gly Tyr Leu Xaa Xaa Xaa Xaa Tyr Tyr Tyr
1               5                   10                  15

Ala Leu Asp Val
            20

<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Arg Asn Tyr Val Tyr
1               5                   10

<210> SEQ ID NO 15
<211> LENGTH: 7
<212> TYPE: PRT
<213> ORGANISM: Homo Sapiens

<400> SEQUENCE: 15

Ser Asn Asn Gln Arg Pro Ser
1               5
```

```
<210> SEQ ID NO 16
<211> LENGTH: 10
<212> TYPE: PRT
<213> ORGANISM: Homo sapiens

<400> SEQUENCE: 16

Ala Ala Trp Asp Ala Ser Leu Arg Gly Val
1               5                   10

<210> SEQ ID NO 17
<211> LENGTH: 10
<212> TYPE: PRT
<213> ORGANISM: Homo sapiens
<220> FEATURE:
<221> NAME/KEY: V-segment
<222> LOCATION: (2)..(2)
<223> OTHER INFORMATION: Xaa is selected from Ala and Ser
<220> FEATURE:
<221> NAME/KEY: V-segment
<222> LOCATION: (4)..(6)
<223> OTHER INFORMATION: Xaa can be any amino acid
<220> FEATURE:
<221> NAME/KEY: V-segment
<222> LOCATION: (7)..(7)
<223> OTHER INFORMATION: Xaa is selected from Leu and Val
<220> FEATURE:
<221> NAME/KEY: V-segment
<222> LOCATION: (9)..(10)
<223> OTHER INFORMATION: Xaa can be any amino acid

<400> SEQUENCE: 17

Ala Xaa Trp Xaa Xaa Xaa Xaa Arg Xaa Xaa
1               5                   10

<210> SEQ ID NO 18
<211> LENGTH: 13
<212> TYPE: PRT
<213> ORGANISM: Homo sapiens

<400> SEQUENCE: 18

Ser Gly Ser Ser Glu Met Thr Val His His Tyr Val Tyr
1               5                   10

<210> SEQ ID NO 19
<211> LENGTH: 12
<212> TYPE: PRT
<213> ORGANISM: Homo sapiens

<400> SEQUENCE: 19

Val Arg Asn Pro Cys Ala Cys Phe Arg Asn Tyr Val
1               5                   10
```

TREATMENT AND PREVENTION OF REMOTE ISCHEMIA-REPERFUSION INJURY

This application is a divisional of application Ser. No. 14/773,020, filed Sep. 4, 2015, which is a national stage filing under 35 U.S.C. § 371 of International Application No. PCT/EP2014/054489, filed on Mar. 7, 2014, which claims priority to European Patent Application No. 13158478.1, filed Mar. 8, 2013. The contents of these applications are each incorporated herein by reference in their entirety.

BACKGROUND OF THE INVENTION

Establishment of a blood-free environment is a prerequisite in reconstructive and orthopedic surgery, which is commonly achieved by tourniquet application. The deprivation of blood and oxygen, termed as ischemia, leads to time-dependent molecular and structural changes of the affected tissue. Complex inflammatory cascades, like the complement, coagulation, as well as the plasma kallikrein-kinin system, are then activated when blood flow is restored, leading to ischemia/reperfusion injury (IRI). Tourniquet-induced IRI is manifested in edema formation, loss of muscle viability and apoptosis, which significantly affects the outcome of surgical interventions. Furthermore, IRI is known to induce a local as well as a systemic inflammatory response leading to remote tissue and organ damage, a phenomenon which is well known in the clinics. Until now, there are no agents available in the clinics to treat local as well as systemic inflammatory responses after IRI (1).

The natural complement inhibitor C1 esterase inhibitor (C1INH) has been demonstrated to inhibit all three complement pathways (classical, lectin as well as the alternative pathway), the coagulation system as well as the kallikrein-kinin system (2-4). Plasma-derived C1INH is successfully used in the clinics to treat C1INH deficient patients suffering from hereditary angioedema (HAE) (2). Several animal studies have demonstrated a therapeutic potential of plasma-derived C1INH on local IRI, namely solid organ transplantation, myocardial infarction, stroke, hepatic and intestinal IRI (4). Two different studies demonstrated a potential therapeutic effect of plasma-derived C1INH on local skeletal muscle IRI, attributing the effect to the complement system (5,6). A study using transgenic mice overexpressing human C1INH with "suprapyhsiologically" high plasma levels showed a reduction of remote organ damage in lung and skeletal muscle in a model of lower torso IRI (7). However, in this model C1INH was constitutively expressed, including during embryonic development, which may lead to changes in the physiology and pathophysiological reactivities. So far, no effect of plasma-derived C1INH on IRI-induced remote tissue or organ damage has been demonstrated.

Surprisingly, using a rat animal model of tourniquet-applied hind limb IRI, the inventors could demonstrate a therapeutic effect of plasma-derived C1INH not only on local but also on remote tissue and organ damage. For example, a significant reduction of lung edema was observed. C1INH plays a major role in inhibiting the contact activation system, and its effect on remote tissue and organ damage indicates a major pathophysiological role of the components of this system not only on local tissue and organ damage but also on the remote damage observed during IRI. The results indicate that substances targeting the contact activation system, such as C1INH, kallikrein inhibitors or Factor XII (FXII) inhibitors, ameliorate or even prevent remote tissue and organ damage.

SUMMARY OF THE INVENTION

The present invention inter alia relates to the subject matter defined in the following items [1] to [32].

[1]. A contact activation system inhibitor selected from the group consisting of a C1 esterase inhibitor (C1INH), a kallikrein inhibitor and a Factor XII (FXII) inhibitor for use in the treatment and/or prevention of remote ischemia-reperfusion injury (IRI), comprising administering the contact activation system inhibitor to an individual.

[2] The contact activation system inhibitor for use according to item [1], wherein the contact activation system inhibitor is a C1INH, preferably human C1INH, more preferably human plasma-derived C1INH or human recombinant C1INH.

[3] The contact activation system inhibitor for use according to item [1], wherein the contact activation system inhibitor is a FXII inhibitor.

[4] The contact activation system inhibitor for use according to any one of the preceding items, wherein the contact activation system inhibitor is administered parenterally to the individual.

[5] The contact activation system inhibitor for use according to any one of the preceding items, wherein the contact activation system inhibitor is administered intravenously, intraarterially or subcutaneously to the individual.

[6] The contact activation system inhibitor for use according to any one of the preceding items, wherein the contact activation system is C1INH and wherein the dose of the C1INH, administered to the individual is from 1 to 5000 IU/kg body weight, preferably from 1 to 1000 IU/kg body weight, more preferably from 10 to 500 IU/kg body weight.

[7] The contact activation system inhibitor for use according to item [6], wherein the dose of the C1INH, administered to the individual is from 10 to 250 IU/kg body weight, preferably from 20 to 100 IU/kg body weight.

[8] The contact activation system inhibitor for use according to item [3] or [4], wherein the contact activation system inhibitor is a FXII inhibitor, and wherein the dose of the FXII inhibitor administered to the individual is suitable for a complete inhibition of the amidolytic activity of FXIIa. Preferably, when the FXII inhibitor is an antibody, the dose administered to the individual is from 0.01 to 50 mg/kg body weight, preferably from 0.1 to 10 mg/kg body weight.

[9] The contact activation system inhibitor for use according to any one of the preceding items, wherein the individual is a patient that is to undergo or has undergone a surgical intervention.

[10] The contact activation system inhibitor for use according to item [9], wherein the contact activation system inhibitor, preferably the C1INH, is administered to the patient within 7 days, preferably within 6 days, more preferably within 5 days, even more preferably within 4 days before the start of the surgical intervention or start of reperfusion. More preferred is an administration within 72 hours, preferably within 48 hours, more preferably within 24 hours, more preferably within 12 hours, even more preferably within 6 hours before start of the surgical intervention or start of reperfusion.

[11] The contact activation system inhibitor for use according to item [9] or item [10], wherein the contact activation system inhibitor, preferably the C1INH, is administered to the patient during the surgical intervention.

[12] The contact activation system inhibitor for use according to any one of items [9] to [11], wherein the contact activation system inhibitor, preferably the C1INH, is administered to the patient after termination of the surgical intervention or after the start of reperfusion.

[13] The contact activation system inhibitor for use according to item [12], wherein the contact activation system inhibitor, preferably the C1INH, is administered to the patient within 72 hours, preferably within 48 hours, more preferably within 24 hours, more preferably within 12 hours, even more preferably within 6 hours or most preferably directly after termination of the surgical intervention or start of reperfusion.

[14] The contact activation system inhibitor for use according to any one of items [9] to [13], wherein the surgical intervention is reconstructive surgery or trauma surgery.

[15] The contact activation system inhibitor for use according to any one of items [9] to [13], wherein the surgical intervention is orthopedic surgery.

[16] The contact activation system inhibitor for use according to item [15], wherein the orthopedic surgery is selected from the group consisting of knee surgery, shoulder surgery and hand surgery.

[17] The contact activation system inhibitor for use according to any one of items [9] to [13], wherein the surgical intervention is transplantation.

[18] The contact activation system inhibitor for use according to item [17], wherein the transplantation is organ, tissue or cell transplantation, preferably of kidney, liver, lung, intestine, pancreas, heart, extremities (e.g. hand), skin or pancreas islet-cells.

[19] The contact activation system inhibitor for use according to any one of items [9] to [13], wherein the surgical intervention is vascular surgery or surgery to treat crash/crush injuries.

[20] The contact activation system inhibitor for use according to any one of items [9] to [13], wherein the surgical intervention is insertion of a device, preferably a catheter, to deliver a pharmacologically active substance, such as a thrombolytic substance or a vasodilator, to the individual, or injection of a pharmacologically active substance such as thrombolytic substance or vasodilator, or insertion of a device for the mechanical removal of a complete or partial vascular obstruction.

[21] The contact activation system inhibitor for use according to item [20], wherein the individual has suffered a myocardial infarction, a stroke, thrombosis, preferably deep vein thrombosis or thrombotic events at foreign surfaces such as stents, thromboembolism, lung embolism, chronic ischemia due to atherosclerosis, preferably chronic limb ischemia due to peripheral atherosclerosis, or other vascular complete or partial obstruction.

[22] The contact activation system inhibitor for use according to item [1] to [8], wherein the remote IRI is due to improvement in the impaired blood flow in the individual that is spontaneous or induced by means other than surgical intervention.

[23] The contact activation system inhibitor for use according to item [22], wherein the administration is prior to reperfusion, e.g. prophylactically, or the administration is as soon as possible after reperfusion occurs.

[24] The contact activation system inhibitor for use according to any one of the preceding items, wherein the contact activation system inhibitor is human C1INH isolated from human plasma.

[25] A method of treating and/or preventing remote ischemia-reperfusion injury (IRI), comprising administering to an individual an effective dose of a contact activation system inhibitor.

[26] A method of preventing ischemia-reperfusion injury (IRI) in a patient that is to undergo or has undergone a surgical intervention, comprising administering to the patient an effective dose of a contact activation system inhibitor prior to and/or during and/or after the surgical intervention, or prior to and/or after start of reperfusion, wherein the ischemia-reperfusion injury (IRI) affects an organ, limb or tissue remote from the site of surgery and/or initial ischemia.

[27] The method of item [25] or [26], wherein the contact activation system inhibitor is selected from the group consisting of a C1INH, a FXII inhibitor, and a kallikrein inhibitor.

[28] The method of item [27], wherein the contact activation system inhibitor is a C1INH, preferably human C1INH, more preferably plasma-derived human C1INH.

[29] The method of item [27], wherein the contact activation system inhibitor is a FXII inhibitor.

[30] The method of any one of items [25] to [29], wherein the remote ischemia-reperfusion injury (IRI) affects the lung, the kidney, the brain, the liver, the heart, the intestine, the pancreas or other organs and extremities.

[31] The method of any one of items [25] to [30], wherein the ischemia-reperfusion injury (IRI) includes multiple organ dysfunction syndrome or systemic inflammatory response syndrome.

[32] The contact activation system inhibitor for use according to item [2], wherein the contact activation system inhibitor is a C1INH, preferably human C1INH, and is combined with a synthetic or natural glycosaminoglycans as e.g. heparin, N-acetylheparin, heparan sulfate, dextran sulfates, dermatan sulfates, and chondroitin sulfates, and/or combined with other substances such as intravenous immunoglobulins, antithrombin III, alpha1 antitrypsin or FXII inhibitor to improve the therapeutic effect. These substances could be administered as a combination therapy or polytherapy.

DETAILED DESCRIPTION

Figure 1:
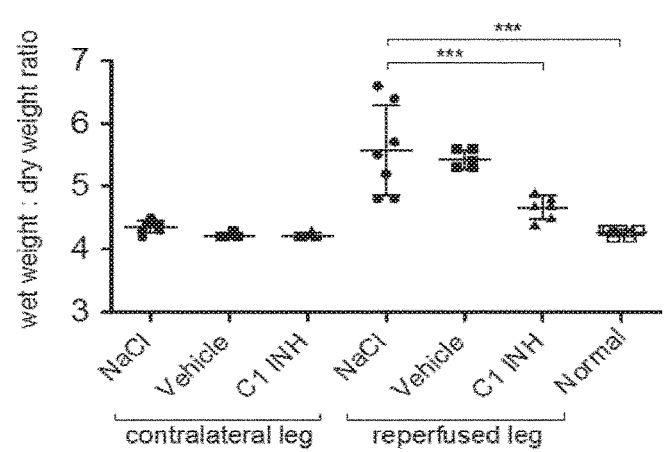
FIG. 1: C1INH significantly prevents local skeletal muscle edema assessed by the wet:dry ratio gastronomic muscle. A: wet:dry ratio analysis. B: Representative picture of non-C1INH treated (left) and C1INH treated limb (right). Each point represents the value of one animal. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, $p<0.05$; , $p<0.01$; *, $p<0.001$.
Figure 1:
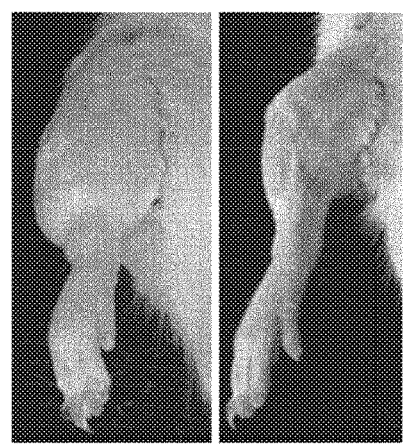

In one aspect, the present invention relates to a contact activation system inhibitor, preferably a C1INH or FXII inhibitor, for use in the treatment and/or prevention of remote ischemia-reperfusion injury (IRI), comprising administering the contact activation system inhibitor, preferably the C1INH or FXII inhibitor, to an individual.

The term "treatment" or "treating" shall be understood to include complete curing of a pathological condition as well as amelioration or alleviation of said condition.

The term "prevention" shall be understood to include complete prevention, prophylaxis, reducing the severity of a pathological condition, as well as lowering the individual's risk of falling ill with said condition. This term shall also be understood to include preconditioning of tissue by administering a contact activation system inhibitor, preferably a C1INH or FXII inhibitor, described herein at a very early stage (e.g. before surgical interventions, before complete diagnosis of remote IRI) so as to prevent the tissue from damages.

The term "individual" refers to a human or animal subject.

The expression "effective amount" is meant to include any amount of an agent according to the present disclosure that is sufficient to bring about a desired therapeutic or prophylactic result, especially upon administration to an individual.

Remote or Distant IRI

As used herein, the term "ischemia-reperfusion injury" (IRI) refers to an injury resulting from the restoration of blood flow to an area of a tissue or organ that had previously experienced deficient blood flow due to an ischemic event.

An IRI can be caused, for example, by a natural event (e.g., restoration of blood flow following a myocardial infarction), a trauma, or by one or more surgical procedures or other therapeutic interventions that restore blood flow to a tissue or organ that has been subjected to a diminished supply of blood. Such surgical procedures include, for example, coronary artery bypass graft surgery, coronary angioplasty, organ transplant surgery and others.

Reperfusion of ischemic tissues results in both a local and a systemic or remote response that, in turn, may result in widespread microvascular dysfunction and altered tissue barrier function. The inflammatory response may even result in the systemic inflammatory response syndrome (SIRS) or the multiple organ dysfunction syndrome (MODS).

As used herein, the phrase "remote IRI" or "distant IRI" or "remote or distant IRI", used interchangeably herein, refers to pathophysiological processes such as thrombotic, thromboembolic and/or inflammatory processes including cellular damage, complement activation and/or edema formation, affecting an organ or tissue which is different from the local ischemic organ(s) and tissue(s) that have been reperfused.

In one embodiment, the remote or distant IRI affects the lung. The remote or distant IRI of this embodiment may include lung edema, thrombotic processes in the lungs, pulmonary embolism and/or inflammation of lung tissue.

In another embodiment, the remote IRI affects the kidney(s). The remote IRI of this embodiment may include renal failure, edema formation, thrombosis, thromboembolism and/or inflammation of renal tissue.

In another embodiment, the remote IRI affects the cardiovascular system. The remote IRI of this embodiment may include myocardial stunning (myocardial dysfunction persisting after reperfusion despite the absence of irreversible damage), thrombosis, reperfusion arrhythmias and/or inflammation/infarction of myocardial tissue.

In another embodiment, the remote IRI affects the gastrointestinal system, preferably the intestine. The remote IRI of this embodiment may include decreased intestinal barrier function, impaired gut motility and absorption, thrombosis, thromboembolism and/or inflammation of gastro-intestinal tissue.

In another embodiment, the remote IRI affects the central nervous system. The remote IRI of this embodiment may include disruption of the blood-brain barrier, silent brain ischemia, stroke, cerebral edema, increased intracranial pressure, and/or inflammation of neuronal tissue.

The remote IRI may be characterized by inflammation, e.g. systemic inflammation. The inflammation may for example affect the lung, the gastrointestinal system, the cardiovascular system, other limbs and/or the central nervous system.

The remote IRI may include systemic inflammatory response syndrome (SIRS) and/or multiple organ dysfunction syndrome (MODS).

The ischemic event preceding the remote IRI may due to a surgery, or due to vascular obstructions not caused by surgery.

Surgical Interventions

In one embodiment, the remote IRI is due to reperfusion of ischemic tissue(s) and/or organs after a surgical intervention. The surgical intervention includes any surgical procedure.

Possible applications in accordance with this invention include preventing remote IRI by administering the contact activation system inhibitor, preferably the C1INH or FXII inhibitor, in conjunction with surgical repair of the thoracic or suprarenal or abdominal aorta due to aneurysmal disease, but also in conjunction with those surgical procedures that induce or require transient occlusion or bypass of the visceral blood supply during and/or following major organ transplant, including liver, kidney, small intestine, extremities and pancreas. Also included is the prevention of remote IRI in conjunction with surgical procedures that result in the transient reduction or prevention of blood flow including hepatic and biliary surgical resections, total or partial pancreatectomy, total and partial gastrectomy, esophagectomy, colorectal surgery, vascular surgery for mesenteric vascular disease, or abdominal insufflation during laparoscopic surgical procedures. Additional applications include blunt or penetrating trauma that results in interruption of blood flow to the visceral organs including those arising from stab wounds or from penetrating wounds or blunt abdominal trauma secondary to motor vehicle accident. Further applications include crush injuries, for example following a natural disaster. Additional applications include insertion of a device for delivery of pharmacologically active substances such as thrombolytic agents or vasodilators and/or for mechanical removal of complete or partial obstructions, and injection of pharmacologically active substances such as thrombolytic agents or vasodilators following onset of an initial thrombotic or thromboembolic or another ischemia-inducing disorder including but not limited to stroke, myocardial infarction, deep vein thrombosis, atherosclerosis or thrombotic events at foreign surfaces.

Preferably, the surgical intervention is selected from the group consisting of orthopedic surgery, vascular surgery, cardiac surgery, catheter-directed procedures, cancer surgery and traumatic surgery. Orthopedic surgery is preferably selected from the group consisting of knee surgery, hand surgery, shoulder surgery, long bones in trauma, hip replacement, and back surgery.

Vascular surgery may be due to repair and/or accidents, for example aortic aneurysms, etc.

In one embodiment, the surgery is traumatic surgery, for example due to car accidents, crash injuries and crush injuries in general, including major trauma with hypovolemia.

In a specific embodiment the surgical intervention is transplantation, preferably of an organ.

Vascular Obstructions not Caused by Surgery

Other preferred applications include diseases or procedures that result in systemic hypotension that either disrupts or decreases the flow of blood to the visceral organs, including hemorrhagic shock due to blood loss, cardiogenic shock due to myocardial infarction or cardiac failure, neurogenic shock, nephrogenic shock, or anaphylaxis.

The remote IRI may be due to improvement in blood flow after ischemia due to hypoperfusion leading to peripheral ischemia with or without organ ischemia.

The remote IRI may also be due to improvement in blood flow after initial thrombotic or thromboembolic processes within a primary organ or tissue, e.g. stroke and myocardial infarction.

In one embodiment, the remote IRI is due to improvement in blood flow after a chronic ischemia event such as chronic limb ischemia due to peripheral atherosclerosis.

Contact Activation System Inhibitors

The term "contact activation system inhibitor" as used herein refers to any compound capable of inhibiting the contact activation system. The contact activation system inhibitor is selected from the group consisting of a C1 esterase inhibitor (C1INH), a Factor XII (FXII) inhibitor, and a kallikrein inhibitor. These inhibitors have the advantage that they act early in the contact activation system pathway, and interact at multiple points in the contact activation system. In contrast, Bradykinin inhibitors, such as Bradykinin receptor antagonists, act at the distal point of the system and the primary point of intervention is at the level of edema formation (cf. Souza et al (10)).

C1 Esterase Inhibitors

C1 esterase inhibitor (C1INH) from human plasma is a glycosylated single chain polypeptide of 478 amino acid residues. The amino acid sequence of human C1INH is shown in SEQ ID NO:1. The average plasma concentration is about 240 µg/mL. Synonyms of C1INH are C1-esterase inhibitor, α2-neuramino-glycoprotein, C1s-inhibitor, and C1-inactivator.

One international unit (IU) of C1INH is defined by comparison to a WHO International Standard C1-inhibitor, plasma. The present, $1^{st}$ International standard is NIBSC code: 08/262, the assigned potency of this preparation is 0.89 IU/ampoule.

As used herein, the term "C1INH" refers to a polypeptide which comprises an amino acid sequence having at least 90% sequence identity to the amino acid sequence as shown in SEQ ID NO:1. For the purpose of the present invention, the degree of identity between two amino acid sequences refers to the percentage of amino acids that are identical between the two sequences. The degree of identity of an amino acid sequence to SEQ ID NO:1 is determined by comparing the amino acid sequence in question and SEQ ID NO 1 using the program "BLAST 2 SEQUENCES (blastp)" (Tatusova et al. (1999) FEMS Microbiol. Lett. 174, 247-250) with the following parameters: Matrix BLOSUM62; Open gap 11 and extension gap 1 penalties; gap x_dropoff50, expect 10.0 word size 3; Filter: none. According to the present invention, the sequence comparison covers at least 400 amino acids, preferably at least 425 amino acids, more preferably at least 450 amino acids, and most preferably at least 475 amino acids.

The C1INH preferably has C1-inhibitory activity that can be assayed as described in Drouet et al. (1988, Clin Chim Acta. 174:121-30). More preferably, the C1INH is a human C1INH having the amino acid sequence as shown in SEQ ID NO:1 (see also UniProt P05155).

In one embodiment, the C1INH has been isolated from human or animal plasma, preferably from human plasma. According to this embodiment the C1INH is preferably glycosylated like native human C1INH.

In another embodiment, the human or animal C1INH is obtained from transfected host cells expressing the C1INH. Such "recombinantly produced" C1INH may be prepared by any suitable method. It may for example be prepared in a recombinant host cell or organism which has been transfected with DNA encoding the C1INH.

C1INH suitable for use in the invention can be obtained from culture medium conditioned by modified cells secreting the protein, and purified by standard methods.

The protein or polypeptide may be obtained by recombinant techniques using isolated nucleic acid encoding the C1INH polypeptide. General methods of molecular biology are described, e.g., by Sambrook et al., Molecular Cloning, A Laboratory Manual, Cold Spring Harbor, N.Y., 2d ed., 1989, and by Ausubel et al., (eds.) Current Protocols in Molecular Biology, New York (1987). The appropriate sequences can be obtained using standard techniques from either genomic or cDNA libraries. Polymerase chain reaction (PCR) techniques can be used. See, e.g., PCR Protocols: A Guide to Methods and Applications, 1990, Innis et al., (Ed.), Academic Press, New York, N.Y. Libraries are constructed from nucleic acid extracted from appropriate cells. Useful gene sequences can be found, e.g., in various sequence databases, e.g., GenBank for nucleic acid and Swiss-Prot for protein.

Standard methods can be used to produce transformed prokaryotic, mammalian, yeast or insect cell lines which express large quantities of the polypeptide. Exemplary mammalian cell lines include COS-7 cells, mouse L cells and CHO cells. See Sambrook (1989), supra and Ausubel et al., 1987, supra.

Various expression vectors can be used to express DNA encoding C1INH. Conventional vectors used for expression of recombinant proteins in prokaryotic or eukaryotic cells may be used.

The C1INH may be produced in soluble form, such as a secreted product of transformed or transfected yeast, insect or mammalian cells. The peptides can then be purified by standard procedures that are known in the art. For example, purification steps could include ammonium sulfate precipitation, ion exchange chromatography, gel filtration, electrophoresis, affinity chromatography, and the like. See Methods in Enzymology Purification Principles and Practices (Springer-Verlag, N.Y., 1982).

Alternatively, C1INH may be produced in insoluble form, such as aggregates or inclusion bodies. The C1INH in such a form is purified by standard procedures that are well known in the art. Examples of purification steps include separating the inclusion bodies from disrupted host cells by centrifugation, and then solubilizing the inclusion bodies with chaotropic agent and reducing agent so that the peptide assumes a biologically active conformation.

The nucleotide sequences used to transfect the host cells can be modified using standard techniques to make C1INH or fragments thereof with a variety of desired properties. Such modified C1INH can vary from the naturally-occurring sequences at the primary structure level, e.g., by amino acid, insertions, substitutions, deletions and fusions. These modifications can be used in a number of combinations to produce the final modified protein chain. The amino acid sequence variants can be prepared with various objectives in mind, including increasing or decreasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants. Such variants can be used in this invention as long as they retain the biological activity of C1INH. The C1INH in accordance with this invention includes the C1INH molecules disclosed in WO2007/073186 and U.S. Pat. No. 8,071,532 B2.

Expression in host cells may result in a C1INH with a modified carbohydrate structure (as compared to the plasma derived C1INH). The C1INH may be modified compared to the plasma derived C1INH in one or more of the following aspects: removal of a carbohydrate moiety (from a naturally occurring variant or recombinantly expressed variant of the glycoprotein), preferably the removal of sialic acid and/or galactose from a N-linked carbohydrate chain and/or the removal of a carbohydrate chain resulting in exposure of mannose, galactose, N-acetylglucosamine and/or fucose residues. Furthermore, modifications of C1INH to increase its plasma half-life are envisaged, for example a fusion with half-life extending moieties such as albumin, immunoglobulin Fc region, or chemical modification such as pegylation or hesylation of C1INH.

Factor XII Inhibitors

The abbreviation "FXII", as used in this application, refers to either or both of Factor XII (FXII) and activated Factor XII (FXIIa). Thus, the term "FXII inhibitor" includes inhibitors of either or both of FXII and FXIIa. Further, anti-FXII antibodies include antibodies that bind to and inhibit either or both of FXII and FXIIa. The term "FXII inhibitor" is also meant to include an inhibitor of FXII that is linked to a half-life extending polypeptide. The FXII inhibitor may be directly linked to the half-life extending polypeptide, or may be linked via a linker, preferably a cleavable linker.

In some embodiments, the FXII inhibitor is a direct inhibitor of FXII. The term "direct" inhibitor means an inhibitor that acts via contact (e.g., binding) with FXII (or FXIIa). In contrast, an indirect inhibitor may act without contacting FXII (or FXIIa) protein; for example, an antisense RNA can be used to decrease expression of the FXII gene or a molecule can inhibit effects of FXIIa via direct interactions with direct downstream FXIIa reaction partners like Factor XI, but it does not interact directly with FXII protein. Thus, an indirect inhibitor, in contrast to a direct inhibitor, acts upstream or downstream from the FXII protein. Some examples of direct inhibitors are presented below. The FXII inhibitors are generally non-endogenous inhibitors; that is, they are not inhibitors that occur naturally in the human or animal body.

A. Infestin-4

In one embodiment, the application provides a FXII inhibitor comprising Infestin domain 4, Infestin-4. In one embodiment, a FXII inhibitor comprises a variant of Infestin-4. In another embodiment, FXII inhibitors comprise Infestin domain 4, and optionally Infestin domains 1, 2, and/or 3; these proteins are known to be potent inhibitors of FXII (see WO 2008/098720; also see FEBS Lett. 512-516, 2004). The wild type polypeptide sequence of Infestin-4 is provided (SEQ ID NO: 2). As used herein, the term "variant" refers to a polypeptide with an amino acid mutation, wherein a "mutation" is defined as a substitution, a deletion, or an addition, to the wild type Infestin-4 sequence, wherein such changes do not alter the functional ability of the polypeptide to inhibit FXII. The term "variant" includes fragments of the wild type or mutated Infestin-4 sequence. Further examples of such variants are provided below.

In one embodiment, an Infestin-4 variant comprises the N-terminal amino acids 2-13 of the wild type Infestin-4 sequence, and at least one and up to five amino acid mutations outside the N-terminal amino acids that result in differences from the wild type Infestin-4 sequence, or six conserved cysteine residues and homology of at least 70% to the wild type Infestin-4 sequence. The N-terminal amino acids 2-13 of the Infestin-4 sequence may be important for binding to FXII based on analysis of structural data for a related inhibitor *Rhodnius prolixus* (PDB: 1 TSO) binding to thrombin, and analysis of SPINK-1 binding to chymotrypsin, which both share a common feature of the accumulation of contact sites in the N-terminal region. Therefore in one embodiment, a variant of Infestin-4 comprises the conserved N-terminal region of amino acids 2-13 of the wild type Infestin-4 sequence, and at least one and up to five amino acid mutations outside these conserved N-terminal amino acids that result in differences from the wild type Infestin-4 sequence. A mutation may be a substitution, a deletion, or an addition. As used herein, the term "outside said N-terminal amino acids" refers to any amino acid along the polypeptide chain of the variant other than the contiguous stretch of amino acids that comprises the sequence VRNPCACFRNYV (SEQ ID NO:19), i.e., amino acids 2-13 from the wild type Infestin-4 sequence. In another embodiment, an Infestin-4 variant comprises six conserved cysteine residues and has homology of at least 70% to the wild type Infestin-4 sequence. In one embodiment, the six conserved cysteine residues are amino acids at positions 6, 8, 16, 27, 31, and 48 of the wild type Infestin-4 sequence. In one embodiment, the variant comprises the final conserved cysteine. In other embodiments, the exact positions of the cysteine residues, and relative positions to each other, may change from positions 6, 8, 16, 27, 31, and 48 of the wild type Infestin-4 sequence due to insertions or deletions in the Infestin-4 variant. Nevertheless, in these embodiments, an Infestin-4 variant comprises all six cysteines and may share 70%, 75%, 85%, 90%, 91%, 92%, 93%, 94%, 95%, 96%, 97%, 98% or 99% homology to the wild type Infestin-4 sequence.

In embodiments, a variant of Infestin-4 is characterized in that it inhibits FXII. The functional activity of inhibiting FXII may be assessed for example, through in vitro and/or in vivo characterization, including direct assays to test inhibition of FXII enzyme activity, prolonged coagulation time, i.e. activated partial thromboplastin time (aPTT), or in vivo methods that evaluate coagulation. Further examples of Infestin-4 variants are SPINK-1 mutants, which are described below.

B. SPINK-1 Mutants

One embodiment involves FXII inhibitors for therapeutic use in humans. A human protein with high similarity to Infestin-4 may be employed. For example, the human protein with the highest similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of serine protease inhibitors. Many proteins from different species have been described (Laskowski M and Kato I, 49 Ann. Rev. Biochem. 593-626, 1980). Based on the wild type SPINK-1 sequence different variants may be generated in order to increase homology of the SPINK-1 sequence to Infestin-4. The phrase "increased homology to Infestin-4" refers to the process whereby amino acid mutations are made to SPINK-1 to bring the SPINK-1 sequence closer to the Infestin-4 sequence.

In one embodiment, SPINK-1 is mutated to comprise the N-terminal amino acids 2-13 of the wild type Infestin-4 sequence; the polypeptide sequence is given and is referred to as K1. As described above, the N-terminal portion of the Infestin-4 sequence is thought to be important for FXII inhibitory function.

Therefore, in one embodiment, a variant of the mutated SPINK-1 also comprises N-terminal amino acids 2-13 of the wild type Infestin-4 sequence, and at least one and up to five amino acid mutations outside said N-terminal amino acids that result in differences from the wild type SPINK-1 sequence and which increase the homology of the variant to the wild type Infestin-4 sequence. In another embodiment, a variant of mutated SPINK-1 comprises six conserved cysteine residues and has homology of at least 70% to the wild type SPINK-1 sequence. A mutation may be a substitution, a deletion, or an addition. As defined above, the term "outside said N-terminal amino acids" refers to any amino acid along the polypeptide chain of the variant other than the contiguous stretch of amino acids that is comprised of the sequence VRNPCACFRNYV (SEQ ID NO:19), i.e., amino acids 2-13 from the wild type Infestin-4 sequence. The term "variant" includes fragments of said mutated SPINK-1 sequence. In one embodiment, the six conserved cysteine residues may be amino acids at positions 9, 16, 24, 35, 38, and 56 of the wild type SPINK-1 sequence. In one embodiment, the variant comprises the final conserved cysteine. In another embodiment, the exact positions of the cysteines, and relative positions to each other, may change from positions 9, 16, 24, 35, 38, and 56 of the wild type SPINK-1 sequence due to insertions or deletions in the SPINK-1 variant. Nevertheless, in these embodiments, a SPINK-1 variant comprises all six cysteines.

In embodiments, a SPINK-1 variant is also characterized in that it inhibits FXII. Further SPINK variants are disclosed in EP 2497489A1 the disclosure of which is incorporated herein in its entirety.

C. Other FXII Inhibitors

In one embodiment, other inhibitors of FXII are administered to a patient receiving a medical procedure. As discussed above, the term inhibitors of FXII includes inhibitors of both FXII and FXIIa. In WO2006/066878 the use of antibodies against FXII or the use of inhibitors of FXII is proposed. Specifically, inhibitors to FXII include antithrombin III (ATM), angiotensin converting enzyme inhibitor, aprotinin, alpha-1 protease inhibitor, antipain ([(S)-1-Carboxy-2-Phenylethyl]-Carbamoyl-L-Arg-L-Val-Arginal), Z-Pro-Proaldehyde-dimethyl acetate, DX88 (Dyax Inc., 300 Technology Square, Cambridge, Mass. 02139, USA; cited in: Williams A and Baird L G, 29 Transfus Apheresis Sci. 255-258, 2003), leupeptin, inhibitors of prolyl oligopeptidase such as Fmoc-Ala-Pyr-CN, com-trypsin inhibitor, mutants of the bovine pancreatic trypsin inhibitor, ecotin, yellowfin sole anticoagulant protein, *Cucurbita maxima* trypsin inhibitor-V including *Cucurbita maxima* isoinhibitors and Hamadarin (as disclosed by Isawa H et al. 277 J. Biol. Chem. 27651-27658, 2002).

In still other embodiments, the FXII inhibitor is H-D-Pro-Phe-Arg-chloromethylketone (PCK). (Tans et al., Eur. J. Biochem. 1987; 164:637-42; Kleinschnitz et al., J Exp Med. 2006; 203:513-8.)

The FXII inhibitor may be for example an analogue of Kunitz Protease Inhibitor domain of amyloid precursor protein as disclosed in U.S. Pat. No. 6,613,890 in columns 4 through 8.

In another embodiment, the FXII inhibitor may be an anti-FXII antibody that binds to FXII and inhibits FXII activation and/or activity. Such an antibody has been described for example in WO 2006/066878, and in Rayon et al., 1 Blood 4134-43, 1995.

Other monoclonal antibodies (mAbs) to human FXII include the B7C9 mAb described by Pixley et al (*J Biol Chem* 1987; 262, 10140-45), a mAb described by Small et al (*Blood* 1985; 65:202-10); the mAbs F1 and F3 described by Nuijens et al (*J. Biol. Chem.* 1989; 264:12941-49); the B6F5, C6B7, and D2E10 mAbs against the light chain of FXII described in WO89/11865; a mAb that selectively binds FXIIa-β over FXII described in WO90/08835; and the anti-FXII antibody OT-2 described in WO91/17258.

Additional preferred anti-FXII/FXIIa monoclonal antibodies and antigen-binding fragment thereof are described in WO 2013/014092, which is incorporated herein by reference. Those antibodies have a more than 2 fold higher binding affinity to human FXIIa-beta than to human FXII and are capable of inhibiting the amidolytic activity of human FXIIa. In some embodiments, the antibody or antigen-binding fragment has one or more of the following features: (a) binds murine FXII/FXIIa; (b) comprises a heavy chain variable (VH) region which is more than 85% identical to the sequence of SEQ ID NO: 7; (c) comprises a light chain variable (vL) region which is more than 85% identical to the sequence of SEQ ID NO: 8; (d) comprises heavy chain CDR1 at least 80% identical to the sequence of SEQ ID NO: 9, and/or heavy chain CDR2 at least 60% identical with SEQ ID NO: 10, and/or heavy chain CDR3 at least 80% identical to the sequence of SEQ ID NO: 12; (e) comprises light chain CDR1 at least 50% identical with SEQ ID NO: 14, and/or light chain CDR2 of SEQ ID NO: 15, and/or light chain CDR3 with the sequence A-$X_1$-W-$X_2$-$X_3$-$X_4$-$X_5$-R-$X_6$-$X_7$ wherein $X_1$ can be A or S, $X_5$ can be L or V, the other $X_n$s can be any amino acid (SEQ ID NO: 17); (f) binds human FXIIa-beta with a $K_D$ of better than $10^{-8}$M, (g) competes with infestin-4, for binding to human FXIIa-beta; or (h) is a human IgG or variant thereof, preferably human IgG4 or variant thereof.

In other embodiments, the anti-FXII antibody is an IgG antibody that binds human FXII and comprises (a) a VH region comprising heavy chain CDR1 as set forth in SEQ ID NO: 9, heavy chain CDR2 as set forth in SEQ ID NO: 11, and heavy chain CDR3 as set forth in SEQ ID NO: 13; and/or (b) a VL region comprising light chain CDR1 as set forth in SEQ ID NO: 14, light chain CDR2 as set forth in SEQ ID NO: 15, and light chain CDR3 as set forth in SEQ ID NO: 17. A heavy chain CDR2 comprising SEQ ID NO: 11 comprises the sequence GI$X_1X_2X_3X_4X_5X_6$TVYADSVKG, wherein $X_1$ is R, N or D, $X_2$ is P, V, I, or M; $X_3$ is S, P, or A; $X_4$ is G, L, V, or T; $X_5$ can be any amino acid, preferably $X_5$ is G, Y, Q, K, R, N, or M; and $X_6$ is T, G, or S. A heavy chain CDR3 comprising SEQ ID NO: 13 comprises the sequence ALPRSGYL$X_1X_2X_3X_4$YYYYALDV, wherein $X_1$ is I, M or V, $X_2$ is S or K; $X_3$ is P, K, T, or H; and $X_4$ is H, N, G, or Q. A light chain CDR3 comprising SEQ ID NO: 17 comprises the sequence A$X_1$W$X_2X_3X_4X_5$R$X_6X_7$, wherein $X_1$ is A or S, $X_2$ is D, Y, E, T, W, E, or S; $X_3$ is A, N, I, L, V, P, Q, or E; $X_4$ is S, D, P, E, Q, or R; $X_5$ is L or V; $X_6$ is G, L, or K; and $X_7$ is V, A, D, T, M, or G.

In other embodiments, the anti-FXII antibody antigen-binding fragment is a fragment of an IgG antibody that binds human FXII and comprises (a) a VH region comprising heavy chain CDR1 as set forth in SEQ ID NO: 9, heavy chain CDR2 as set forth in SEQ ID NO: 10, and heavy chain CDR3 as set forth in SEQ ID NO: 12; and/or (b) a VL region comprising light chain CDR1 as set forth in SEQ ID NO: 14, light chain CDR2 as set forth in SEQ ID NO: 15, and light chain CDR3 as set forth in SEQ ID NO: 16.

In one embodiment, the anti-FXII antibody or antigen-binding fragment thereof is the antibody "3F7" used in Example 3. Sequences of the variable regions and CDRs of 3F7 are presented in Table 1.

TABLE 1

| Region | Amino acid sequence |
|---|---|
| VH | EVQLLESGGGLVQPGGSLRLSCAASGFTFSKYI MQWVRQAPGKGLEWVSGIRPSGGTTVYADSVKG RFTISRDNSKNTLYLQMNSLRAEDTAVYYCARA LPRSGYLISPHYYYYALDVWGQGTTVTVSS (SEQ ID NO: 7) |

TABLE 1-continued

| Region | Amino acid sequence |
|---|---|
| VL | QSELTQPPSASGTPGQRVTISCSGSSSNIGRNY VYWYQQVPGTAPKLLIYSNNQRPSGVPDRFSGS KSGTSASLVISGLRSEDEADYYCAAWDASLRGV FGGGTKLTVLG (SEQ ID NO: 8) |
| HCDR 1 (Kabat 31-35) | KYIMQ (SEQ ID NO: 9) |
| HCDR 2 (Kabat 50-65) | GIRPSGGTTVYADSVKG (SEQ ID NO: 10) |
| HCDR 3 (Kabat 95-102) | ALPRSGYLISPHYYYYALDV (SEQ ID NO: 12) |
| LCDR 1 (Kabat 24-34) | SGSSSNIGRNYVY (SEQ ID NO: 14) |
| LCDR 2 (Kabat 50-56) | SNNQRPS (SEQ ID NO: 15) |
| LCDR 3 (Kabat 89-97) | AAWDASLRGV (SEQ ID NO: 16) |

In still other embodiments, the anti-FXII antibody or antigen binding fragment is chosen from the affinity matured (relative to 3F7) antibodies VR115, VR112, VR24, VR110, VR119.

TABLE 2

| mAb | HCDR1 | HCDR2 | HCDR3 | LCDR1 | LCDR2 | LCDR3 |
|---|---|---|---|---|---|---|
| 3F7 | 9 | 10 | 12 | 14 | 15 | 16 |
| VR119 | 9 | 11 | 12 | 14 | 15 | 16 |
| VR112 | 9 | 11 | 12 | 14 | 15 | 16 |
| VR115 | 9 | 11 | 12 | 14 | 15 | 16 |
| VR24 | 9 | 10 | 12 | 18 | 15 | 16 |
| VR110 | 9 | 11 | 12 | 14 | 15 | 16 |

As noted above SEQ ID NO: 11 is a degenerate sequence. VR119 comprises SEQ ID NO: 11 wherein $X_1$ is N, $X_2$ is V, $X_3$ is P, $X_4$ is L, $X_5$ Y; and $X_6$ is G. VR112 comprises SEQ ID NO: 11 wherein $X_1$ is N, $X_2$ is V, $X_3$ is P, $X_4$ is V, $X_5$ is Q, and $X_6$ is G. VR115 comprises SEQ ID NO: 11 wherein $X_1$ is D, $X_2$ is I, $X_3$ is P, $X_4$ is T, $X_5$ is K, and $X_6$ is G. VR110 comprises SEQ ID NO: 11 wherein $X_1$ is D, $X_2$ is M, $X_3$ is P, $X_4$ is T, $X_5$ is K, and $X_6$ is G. VR24 comprises a unique LCDR1: SGSSEMTVHHYVY (SEQ ID NO: 18).

In embodiments involving antibody CDRs, CDR's are defined according to the KABAT numbering system. (Kabat E A, Wu T T, Perry H M, Gottesman K S, Foeller C (1991) Sequences of proteins of immunological interest, 5th edn. U.S. Department of Health and Human services, NIH, Bethesda, Md.)

In some embodiments, the antibody or antigen-binding fragment thereof is an anti-FXII/FXIIa monoclonal antibody or antigen-binding fragment thereof that inhibits FXIIa-alpha by more than 40%, more than 50%, or more than 60%, when used at a molar ratio of FXIIa-alpha to antibody of 1:0.2. In some embodiments, the antibody or antigen binding fragment thereof inhibits FXIIa-alpha by more than 80%, more than 85%, or more than 90%, at a molar ratio of FXIIa-alpha to antibody of 1:0.5. In one embodiment, the antibody achieves complete inhibition of FXIIa-alpha at a molar ratio of 1:0.5. In one embodiment, the FXIIa-alpha is human FXIIa-alpha. In one embodiment, the antibody or antigen binding fragment thereof has an affinity for human FXIIa that is at least comparable to antibody 3F7.

As discussed above, an "anti-FXII antibody" includes antibodies that bind to and inhibit either or both of FXII and FXIIa. In one embodiment, the antibody may be in the form of a full length Ig, Fab, F(ab)$_2$, Fv, scFv, or other form or variant thereof. The antibody may be monoclonal or polyclonal. The antibody may be characterized in that the isotype is IgM, IgD, IgA, IgG, or IgE, or any subclass thereof, such as IgG$_1$, or variants thereof. The antibody may be from a mammalian species, including, but not limited to human, mouse, rat, rabbit, goat, hamster, or monkey. The antibody may be humanized or CDR-grafted. The antibody may be mutated or modified to alter immunogenicity, half-life, or to impart other advantageous properties associated with a therapeutic antibody. In one embodiment, the antibody is an anti-FXII antibody that binds to an epitope on the heavy chain or light chain of FXII (wherein, "FXII" includes FXII and FXIIa), such as a neutralizing epitope. The antibody may be high affinity and/or high avidity for binding to FXII. The antibody may be conjugated to a polypeptide, nucleic acid or small molecule.

D. FXII Inhibitors Linked to Half-Life Extending Moieties

Polypeptides

Another aspect of the application provides FXII inhibitors linked to a half-life enhancing polypeptide (HLEP). For example, in one embodiment, FXII inhibitors are linked to half-life extending proteins. A "half-life enhancing polypeptide" increases the half-life of the FXII inhibitor in vivo in a patient or in an animal. For example, albumin and immunoglobulins and their fragments or derivatives have been described as half-life enhancing polypeptides (HLEPs). Ballance et al. (WO 2001/79271) described fusion polypeptides of a multitude of different therapeutic polypeptides which, when fused to human serum albumin, are predicted to have an increased functional half-life in vivo and extended shelf life. The embodiments relating to FXII inhibitors linked to half-life enhancing polypeptides disclosed in EP 2497489 A1 can be used in accordance with the present invention and are incorporated herein by reference.

E. Linkers

In one embodiment, an intervening peptidic linker may be introduced between the therapeutic polypeptide and the HLEP. In one embodiment, a cleavable linker is introduced, particularly if the HLEP interferes with the therapeutic polypeptide's specific activity, e.g. by steric hindrance. In certain embodiments, the linker is cleaved by enzymes such as coagulation proteases of the intrinsic, extrinsic, or common coagulation pathway. Coagulation proteases of the intrinsic pathway are proteases in the contact activation pathway, including, for example, FXIIa, FXIa, or FIXa. In one embodiment, the linker is cleaved by FXIIa. Proteases of the extrinsic pathway include proteases in the tissue factor pathway, for example, FVIIa. Proteases of the common pathway includes proteases involved in the conversion of fibrinogen to fibrin, for example, FXa, FIIa, and FXIIIa.

Combinations/Kits

Another aspect of the invention is the combination of C1INH with agents. Preferably C1INH may be administered combined with a synthetic or natural glycosaminoglycans as e.g. heparin, N-acetylheparin, heparan sulfate, dextran sulfates, dermatan sulfates, and chondroitin sulfates which are known to potentiate the activity of C1INH. In addition, C1INH may be combined with other substances including, but not limited to, intravenous immunoglobulins, antithrombin III, alpha1 antitrypsin or FXII inhibitor, to improve the therapeutic effect. These substances could be administered as a combination therapy or polytherapy. Therefore, kits comprising C1INH and one or more of the substances mentioned above, for the use in prevention and/or treatment of remote IRI including instructions for administration are also aspects of the invention. An embodiment of the invention is therefore a kit of parts comprising C1INH and at least one other substance as listed above for the simultaneous, separate or sequential use in the prevention and/or treatment of remote IRI.

Administration

The contact activation system inhibitor, preferably the C1INH or FXII inhibitor, described herein is preferably administered as part of a pharmaceutical composition comprising the contact activation system inhibitor, preferably the C1INH or FXII inhibitor, and a pharmaceutically acceptable excipient. The pharmaceutical composition can be easily administered parenterally such as for example, by intravenous, intraarterial, intramuscular, intraperitoneal, intrathecal, intranasal, intrapulmonal, dermal or subcutaneous application. Parenteral administration can be accomplished by incorporating the compositions of the present invention into a solution, emulsion or suspension.

Preferably, the composition comprising the contact activation system inhibitor, preferably the C1INH or FXII inhibitor, is administered intravenously, intraarterially, or subcutaneously either by single or multiple bolus-injection(s) and/or by continuous infusion or infusions over a certain period of time.

Alternatively, the pharmaceutical composition could be administered enterally such as for example, by oral or rectal application.

The dose of the C1INH to be administered to the individual ranges from 1 to 5000 IU/kg body weight. Preferably, the dose is within the range from 1 to 2500 IU/kg, more preferably from 1 to 500 IU/kg, even more preferably from 10 to 500 IU/kg body weight. Most preferably, the dose ranges from 10 IU/kg to 250 IU/kg body weight, or even from 20 IU/kg to 100 IU/kg body weight. The skilled person will be aware of the need to adjust the dose depending on various factors, such as route of administration.

The dose range of FXII inhibitors is adjusted according to the type of inhibitor used, route of administration and other factors the skilled person will be well aware of. The dose and dosing interval is preferably chosen so that the amidolytic activity of FXIIa is completely inhibited for the desired period of treatment. For example, a FXII inhibitory antibody would be administered in a dose ranging from 0.01 to 50 mg/kg body weight, from about 0.01 to 30 mg/kg, from about 0.1 to 30 mg/kg, from about 0.1 to 10 mg/kg, from about 0.1 to 5 mg/kg, from about 1 to 5 mg/kg, from about 0.1 to 2 mg/kg or from about 0.1 to 1 mg/kg. The treatment may comprise giving a single dose or multiple doses. If multiple doses are required, they may be administered daily, every other day, weekly, biweekly, monthly, or bimonthly or as required. A depository may also be used that slowly and continuously releases the antibody or antigen-binding fragment thereof. A therapeutically effective dose may be a dose that inhibits FXIIa in the subject by at least 50%, preferably by at least 60%, 70%, 80%, 90%, more preferably by at least 95%, 99% or even 100%.

In case of an infestin-based FXII inhibitor, e.g. albumin-fused infestin-4, the dose may be between 0.1 and 1000 mg/kg body weight, preferably between 1 and 1000 mg/kg, more preferably between 1 and 500 mg/kg, even more preferably between 50 and 500 mg/kg.

For these and other FXII inhibitors, the skilled person will be able to adjust the dose as required by the treatment, and will be aware of the factors influencing the required dose, such as route of administration, half-life of the inhibitor, inhibitory activity of the inhibitor, affinity to FXIIa of the inhibitor and such like.

For the treatment of remote or distant IRI caused by therapeutic interventions, such as surgical procedures, it is preferable that the contact activation system inhibitor, preferably the C1INH or FXII inhibitor, is administered to an individual undergoing treatment prior to the surgical intervention (e.g. limb surgery, cardiac surgery, organ transplantation, etc.). In one aspect, the contact activation system inhibitor, preferably the C1INH or FXII inhibitor, is therefore administered to the individual prior to the start of a surgical intervention.

The contact activation system inhibitor, preferably the C1INH or FXII inhibitor, may be administered to the patient within one week, 6 days, 5 days, 4 days, or 72 hours, preferably within 48 hours, more preferably within 24 hours prior to start of the surgical intervention, even more preferably within 12 hours, most preferably within 6 hours before the start of the surgical intervention.

For example, the contact activation system inhibitor, preferably the C1INH or FXII inhibitor, can be administered to an individual undergoing treatment, e.g., about 1 hour, about 2 hours, about 3 hours, about 4 hours, about 5 hours, about 12 hours, about 24 hours, about 36 hours, about 48 hours or about 72 hours prior to the surgical intervention. The contact activation system inhibitor, preferably the C1INH or FXII inhibitor, can also be administered to an individual undergoing treatment, for example, about 5 minutes, about 10 minutes, about 15 minutes, about 20 minutes, about 30 minutes or about 45 minutes prior to the therapeutic intervention.

Alternatively, or in addition, the contact activation system inhibitor, preferably the C1INH or FXII inhibitor, can be administered to an individual undergoing treatment at the time of, or during, the surgical intervention. In another embodiment, the contact activation system inhibitor, preferably the C1INH or FXII inhibitor, is therefore administered to the patient during the surgical intervention. For example, the contact activation system inhibitor, preferably the C1INH or FXII inhibitor, can be administered one or more times during the course of a surgical intervention in intervals (e.g., 15 minute intervals). Alternatively, the contact activation system inhibitor, preferably the C1INH or FXII inhibitor, can be administered continuously throughout the duration of a therapeutic intervention.

Furthermore, the contact activation system inhibitor, preferably the C1INH or FXII inhibitor, can be administered to an individual undergoing treatment after a surgical intervention. In yet another embodiment, the contact activation system inhibitor, preferably the C1INH or FXII inhibitor, is administered to the patient after termination of the surgical intervention, preferably within a period of 72 hours after termination of the surgical intervention. For example, the contact activation system inhibitor, preferably the C1INH or FXII inhibitor, can be administered to a subject undergoing treatment, e.g., about 1 hour, about 2 hours, about 3 hours, about 4 hours, about 5 hours, about 12 hours, about 24 hours, or about 48 hours after the surgical intervention. The contact activation system inhibitor, preferably the C1INH or FXII inhibitor, can also be administered to a subject undergoing treatment, for example, about 5 minutes, about 10 minutes, about 15 minutes, about 20 minutes, about 30 minutes or about 45 minutes after the surgical intervention. Preferably, the contact activation system inhibitor, preferably the C1INH or FXII inhibitor, is administered as soon as possible after the surgical intervention, and treatment is maintained for at least 24 hours, preferably at least 48 hours, more preferably at least 72 hours after the surgical intervention or longer if required.

In yet another embodiment, the contact activation system inhibitor, preferably the C1INH or FXII inhibitor, is administered to the patient during the surgical intervention and after termination of the surgical intervention.

In a further embodiment, the contact activation system inhibitor, preferably the C1INH or FXII inhibitor, is administered to the patient prior to the start of the surgical intervention, during the surgical intervention and after termination of the surgical intervention.

In a further embodiment, the contact activation system inhibitor, preferably the C1INH or FXII inhibitor, is administered to the patient prior to the start of the surgical intervention and after termination of the surgical intervention, but not during the surgical intervention.

In a further embodiment, the contact activation system inhibitor, preferably the C1INH or FXII inhibitor, is administered to the patient prior to the start of the surgical intervention and during the surgical intervention, but not after termination of the surgical intervention.

In a further embodiment, the contact activation system inhibitor, preferably the C1INH or FXII inhibitor, is administered prior to the start of reperfusion. Preferably, the contact activation system inhibitor, preferably the C1INH or FXII inhibitor, is administered up to one week prior to reperfusion, up to 6 days, 5 days, 4 days, preferably up to 72 hours, more preferably up to 48 hours, even more preferably up to 24 hours, up to 12 hours, most preferably up to 6 hours prior to reperfusion.

In yet a further embodiment, the contact activation system inhibitor, preferably the C1INH or FXII inhibitor, is administered after the start of reperfusion. Preferably, the contact activation system inhibitor, preferably the C1INH or FXII inhibitor, is administered up to 72 hours after the start of reperfusion, more preferably up to 48 hours, up to 12 hours, even more preferably up to 6 hours, most preferably immediately after the start of reperfusion.

In a preferred embodiment, the contact activation system inhibitor, preferably the C1INH or FXII inhibitor, is administered prior to the start of reperfusion and after the start of reperfusion. Preferably, the contact activation system inhibitor, preferably the C1INH or FXII inhibitor, is administered up to one week prior to reperfusion, up to 6 days, 5 days, 4 days, preferably up to 72 hours, more preferably up to 48 hours, even more preferably up to 24 hours, up to 12 hours, most preferably up to 6 hours prior to reperfusion, and the treatment is then maintained for a period after the start of reperfusion, preferably at least for 72 hours, more preferably for at least 4 days, even more preferably for at least one week, most preferably for 2 weeks or longer if required.

In a specific embodiment, the contact activation system inhibitor, preferably the C1INH or FXII inhibitor, is administered to the patient for less than 1 month, preferably for less than 14 days, more preferably for less than 7 days, most preferably for less than 48 hours.

Examples

Materials and Methods

Animals and Housing

All Experiments were conducted under the term of the Swiss Animal Protection Law and were approved by the animal ethics committee of the cantonal veterinary service (Cantone of Bern, Switzerland). Male Wistar rats (wild type, internal animal facility, University of Bern) were kept at three per cage under standard housing conditions with food and water ad libitum. Animals were housed in thermoneutral environment of 20±2° C. and indoor humidity of 45%-65% controlled rooms in which a circadian rhythm of 12/12 h (based on winter time) was maintained. During the light cycle animals were exposed to an intensity of 200 lux.

Reagents

C1INH (Berinert®) and the vehicle (10 mg/mL glycine, 2.9 mg/mL sodium citrate and 8.5 mg/mL sodium chloride) were provided by CSL Behring AG (Bern, Switzerland). C1INH was administered as a bolus via the tail vein by using an I.V. cannula (BD Vasculon Plus) 5 minutes before induction of ischemia.

FXIIa inhibitor rHA-Infestin-4 (Hagedorn et al, 2010, Circulation 121:1510-1517) is administered as a bolus via the tail vein at a dose of 100 mg/kg 5 minutes before induction of ischemia.

Surgical Procedure

Male Wistar rats weighing between 250 and 350 g were used for the following experiments. Induction of anesthesia was performed with 2.5% isoflurane in oxygen in an anesthetic induction chamber and later maintained by inhalation of 1.5% isoflurane via a nose mask. For assessment of limb perfusion the fur was completely removed from both hind limbs with an electric shaver. The rats were kept on a heating pad to maintain the body temperature at 37° C. Approximately, thirty min after the induction of anesthesia, unilateral hind limb ischemia was induced for 3 h. Ischemia was induced by clamping the femoral artery. Therefore, an incision in the groin area was conducted, the fatty tissue was carefully removed and the femoral vessels were exposed. Next the femoral artery was isolated from the vein.

Before clamping the artery a tourniquet (standardized weight of 450 g) was placed underneath the femoral vessels like described before (8). The femoral artery was transiently occluded with two microvascular clamps (B1-V, S&T Switzerland). Immediately, the tourniquet was tightened to block microvascular blood flow. During the whole procedure the hemodynamics were monitored (Mouse ox plus, Starlifesciences). After 3 hours of ischemia the limb was reperfused for 24 hours, respectively. During 24 hours reperfusion rats woke up and were treated with analgesia (Buprenorphine, 0.05 mg/kg, Temgesic Reckitt Benckiser (Switzerland AG)). At the end of the experiment, the lung as well as both the ischemic and contralateral gastrocnemic muscles were taken for analysis.

Assessment of Edema Formation

For assessment of edema formation two samples of the gastrocnemic muscle from both legs were taken and immediately weighed to obtain the wet weight. The muscle samples or lungs were dried for 24 hours at 80° C. until a constant weight could be achieved. In a second weighing step the dry weight was obtained. Subsequently, the wet weight to dry weight ratio was calculated and compared with the wet to dry weight ratio of the contralateral control muscle.

Determination of Deposited Complement Components and Other Proteins in Muscle and Lung Tissue Immunofluorescence (IF) was used to quantify the deposition of various components of the complement system as well as Fibrin/Fibrinogen, Heparan Sulfate, Bradykinin receptor $B_1$ and Bradykinin receptor B2. Tissue sample from the gastrocnemic muscle of both legs and the lung were taken, washed in PBS, blotted dry and embedded in matrix (OCT, Tissue tek) on dry ice. Immediately, the samples were stored at −20° C. until cryosections were cut (Cryostat, Leica CM 3050S). Sections were fixed with acetone and rehydrated in TBS. Primary antibodies were incubated over night at 4° C. and the following secondary antibodies were incubated for 1 hour at room temperature. Subsequently, slides were mounted and covered. Pictures were taken with the fluorescent microscope (Leica) and analyzed by using Image J software.

Cytokine/Chemokine Measurement Using Multiplex Array

A multiplex immunoassay consisting of magnetic beads conjugated with a capture antibody specific for a target protein was used to detect an array of cyto- and chemokines (Bioplex Pro™ Rat Cytokine Group I panel, BioRad, Hercules, USA). The assay was performed according to manufacturer's instructions.

Briefly, plasma was diluted 1:3 and incubated with antibody-coupled magnetic beads. A washing step was followed by incubation with biotinylated detection antibody. After streptavidin-phycoerythrin incubation the concentration of cytokines/chemokines was measured. Recombinant cytokines/chemokines were used to establish standard curves. Analyte concentrations were calculated using the Bio-Plex Manager 4.0 Software (Bio-Rad, Hercules, USA).

Assessment of Apoptosis by TUNEL Assay

Apoptosis was assessed by using a TdT-mediated dUTP nick end-labeling (TUNEL) assay (in situ Cell Death Detection Kit, TMR red, Roche, Mannheim, Germany). In brief, cryosections of tissue samples were fixed in acetone for 5 minutes at room temperature, washed and permeabilized with 0.1% Triton-X-100 on ice. Sections were incubated with TUNEL reaction mixture for 1 h at 37° C. in the dark and counterstained with DAPI. After a washing step sections were mounted, coverslipped and analyzed with a fluorescent microscope. Immunofluorescence images were analyzed with image J (National Institutes of Health, Bethesda, Md., USA). The area in % covered by TUNEL-positive nuclei was analyzed and calculated in relation to the area covered by all DAPI-stained nuclei.

Statistical Analysis

Data are expressed as means±SD. Statistical significance was determined by one-way analysis of variance with Dunnetts post-test using the GraphPad Prism 5 software. P values<0.05 were considered statistically significant.

Results i) Effect of C1INH on Local IRI Tissue Damage

C1INH Prevented Local IRI Induced Skeletal Muscle Edema

As a first step, the therapeutic effect of C1INH (50 IU/kg) was assessed by prevention of local edema formation in the hind limb. Systemic preload of the animal with human plasma-derived C1INH highly significantly prevented the formation of skeletal muscle edema (see FIGS. 1A and B). Similar results, i.e. reduction in muscle edema formation, are expected using a FXII inhibitor eg. a monoclonal anti-FXII antibody or rHA-Infestin-4.

ii) Effects of C1INH on IRI Induced Remote Tissue and Organ Damage

C1INH Inhibited Remote Organ Damage by Attenuating Lung Edema

Figure 2:
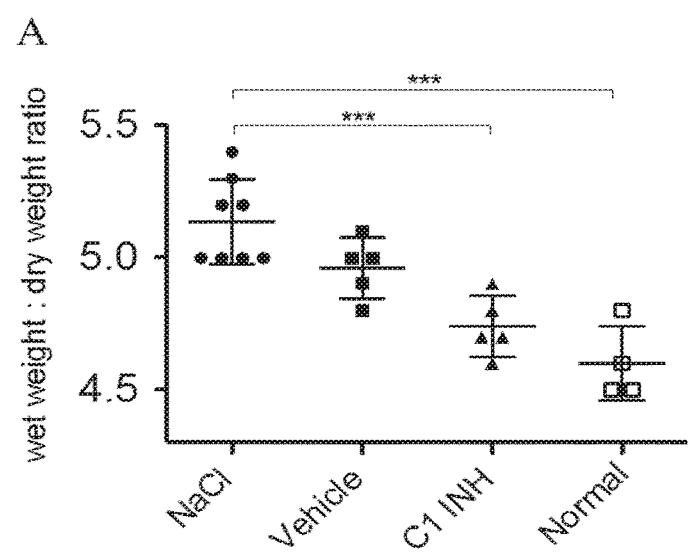
FIG. 2: C1INH significantly prevents remote lung edema. Each point represents the value of one animal. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, $p<0.05$; , $p<0.01$; *, $p<0.001$.

The effect of C1INH on remote tissue and organ damage was analyzed. C1INH is a very potent inhibitor the plasma kallikrein-kinin system by interacting with FXIIa and kallikrein. As shown in FIG. 2, C1INH significantly prevented the formation of edema as analyzed by the wet:dry ratio and therefore endothelial cell integrity in the lung was preserved.

Effect of C1INH on the Expression of Bradykinin Receptors in the Lung and the Heart Activation of plasma kallikrein-kinin system results in the generation of bradykinin.

Figure 3:
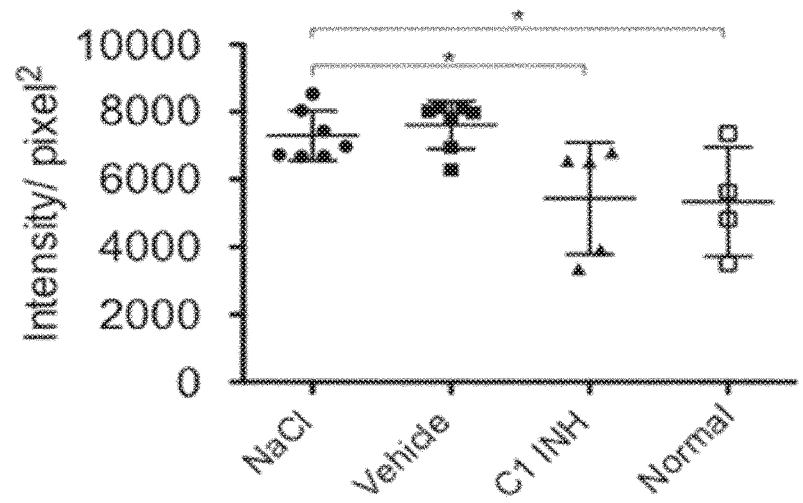
FIG. 3: Effect of C1INH on the expression of the bradykinin receptors $B_1R$ and $B_2R$ in lungs analyzed by IF. A: $B_1R$ expression. B: $B_2R$ expression. Each point represents the value of one animal. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, p<0.05; , p<0.01; *, p<0.001.
Figure 3:
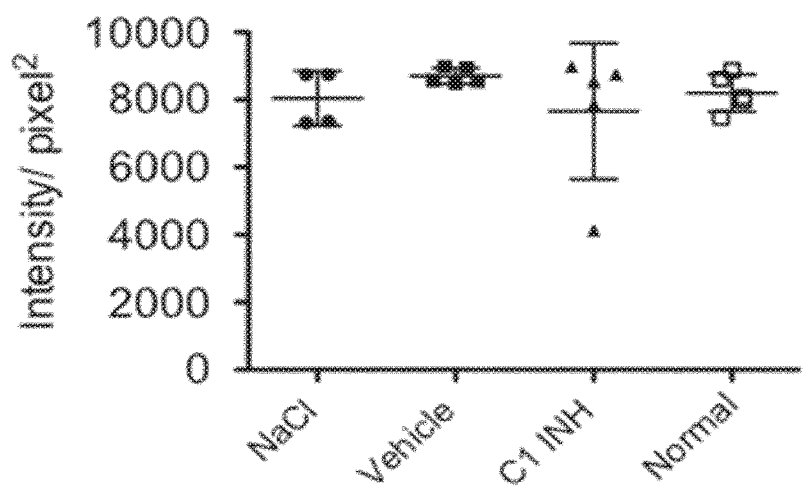
Figure 7:
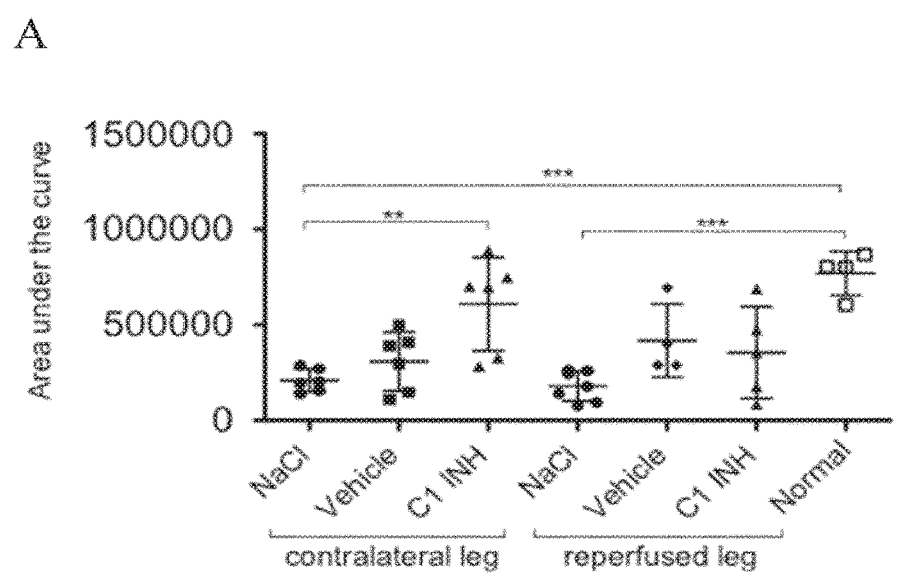
FIG. 7: Shedding of heparan sulfate is attenuated by C1INH in the contralateral limb. Each point represents the value of one animal. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, p<0.05; , p<0.01; *, p<0.001.

This molecule is a very potent vasoactive peptide inducing vasodilation and edema. The kallikrein-kinin system has been shown to be a crucial player of IRI. An antagonist of the bradykinin 2 receptor ($B_2R$) has been successfully used in the clinics to treat HAE patients (9). The effect of C1INH on $B_1R$ and $B_2R$ expression was analyzed by IF. Surprisingly, C1INH significantly inhibited IRI induced upregulation of $B_1R$ in lung tissue (see FIG. 3A) whereas no inhibition could be observed for the expression of $B_2R$ (see FIG. 3B). The same effect was observed in heart tissue (data not shown).

coagulant and anti-inflammatory properties of the endothelium. HS are rapidly released under conditions of inflammation and tissue damage (11-14). Surprisingly, C1INH prevented shedding of HS in the contralateral limb (see FIG. 7).

Inhibitory Effect of C1INH on the Inflammatory Cytokine and Chemokine Network

Cytokines, growth factors as well as chemokines were measured using xMAP technology in EDTA-plasma taken at baseline, i.e. before induction of ischemia and at the endpoint after 24 h reperfusion. Analysis revealed C1INH treatment significantly reduced the levels of IL-1α, IL-4, IL-7, IL-17A and IL-18 as well as IFN-γ, MIP-1α, MIP-3α and TNF-α (see Table 3).

TABLE 3

| Marker | Baseline (in pg/ml) | Group NaCl (in pg/ml) | Group C1 INH (in pg/ml) | p-Value |
|---|---|---|---|---|
| EPO | 278.9 ± 183.2 | 729 ± 427.7 | 346.9 ± 353.1 | n.s |
| GRO/KC | 93.0 ± 14.491 | 127.4 ± 77.02 | 78.27 ± 68.79 | n.s |
| IFN-γ | 57.61 ± 34.88 | 120.3 ± 100.2 | 19.06 ± 11.42 | P < 0.05 (*) |
| IL-1α | 8.97 ± 4.923 | 83.06 ± 44.86 | 16.85 ± 10.27 | P < 0.05 (*) |
| IL-4 | 22.62 ± 11.40 | 57.52 ± 39.27 | 8.343 ± 4.209 | P < 0.05 (*) |
| IL-5 | 96.48 ± 11.16 | 172.7 ± 73.59 | 108.3 ± 23.67 | n.s |
| IL-7 | 69.05 ± 22.87 | 240.9 ± 98.34 | 67.21 ± 42.01 | P < 0.01 (**) |
| IL-10 | 306.6 ± 51.34 | 776.3 ± 508.0 | 279.1 ± 94.20 | n.s |
| IL-17A | 7.02 ± 1.473 | 27.08 ± 13.97 | 8.267 ± 3.391 | P < 0.05 (*) |
| IL-18 | 1103 ± 720.6 | 4155 ± 1390 | 1115 ± 580.4 | P < 0.01 (**) |
| MCP-1 | 425 ± 57.98 | 1693 ± 982.4 | 1905 ± 638.3 | n.s |
| MIP-1α | 1097 ± 968.0 | 4629 ± 3045 | 1203 ± 762.0 | P < 0.05 (*) |
| MIP-3α | 9.98 ± 8.583 | 47.97 ± 20.24 | 12.02 ± 9.502 | P < 0.05 (*) |
| RANTES | 164 ± 89.06 | 310.2 ± 309.7 | 389 ± 442.7 | n.s |
| TNF-α | 19.12 ± 6.099 | 40.38 ± 24.88 | 9.147 ± 7.453 | P < 0.05 (*) |
| VEGF | 11.97 ± 4.891 | 16.02 ± 6.045 | 11.44 ± 2.021 | n.s |
| M-CSF | 293.6 ± 50.83 | 381.2 ± 117.1 | 459.1 ± 79.21 | n.s |

C1INH Inhibited Fibrin Deposition in the Lung

Figure 4:
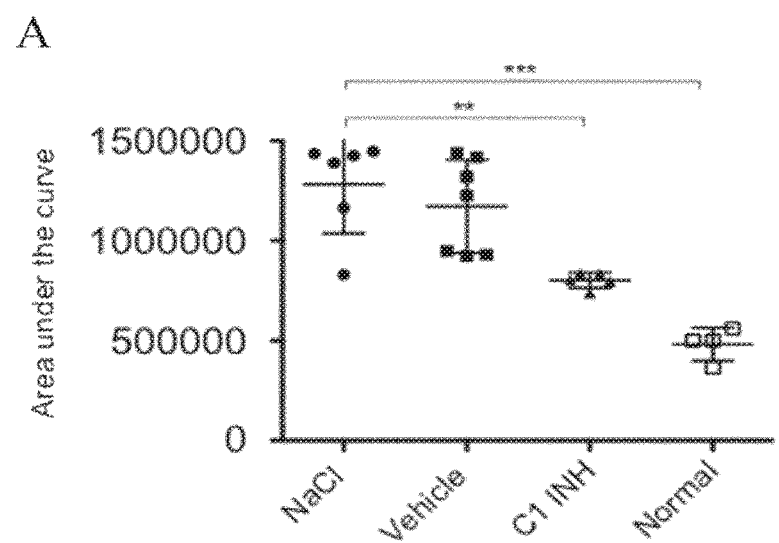
FIG. 4: C1INH prevents deposition of fibrin in the lung. Each point represents the value of one animal. Horizontal bar shows the mean of the different animals. Statistical significance was determined by one-way analysis of variance with Dunnetts post-test using the GraphPad Prism 5 software. Mean±SD data are shown. Statistical significance between samples was indicated as follows *, p<0.05; , p<0.01; *, p<0.001.

Beside complement inhibition, C1INH acts on the coagulation system by interaction with FXII and FXI. Activation of the coagulation system results in the generation of thrombin which cleaves fibrinogen into fibrin. Treatment with C1INH significantly inhibited fibrin deposition in the lung tissue (see FIG. 4).

Figure 5:
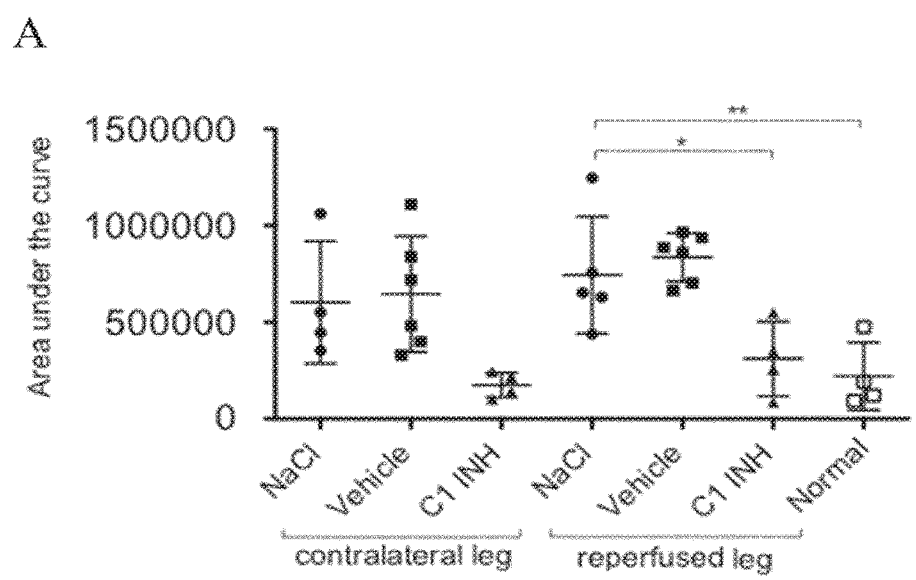
FIG. 5: C1INH reduces fibrin deposition in the contralateral leg. Each point represents the value of one animal. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, p<0.05; , p<0.01; *, p<0.001.

C1INH Prevented Remote Tissue Damage in the Contralateral Limb by Preventing Fibrin Deposition As described above, we could not detect edema formation in the non-ischemic contralateral limb. Surprisingly, we could observe fibrin deposition in the contralateral leg (see FIG. 5). As observed in the lung (see FIG. 4A), we observed a significant inhibition of fibrin deposition in the non-ischemic limb by C1INH (see FIG. 5).

Figure 6:
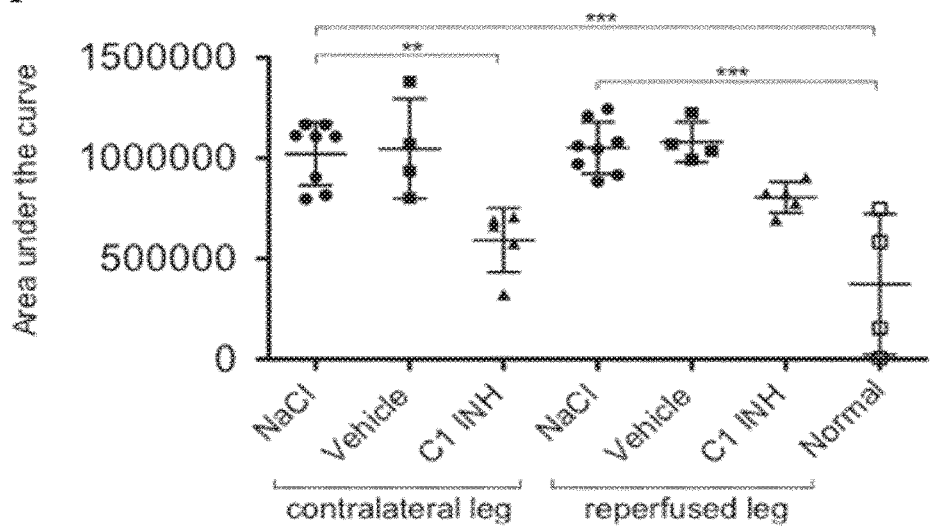
FIG. 6: C1INH inhibits C3b and factor B deposition in the contralateral limb. Each point represents the value of one animal. A: C3b deposition. B: factor B deposition. Horizontal bar shows the mean of the different animals. Mean±SD data are shown. Statistical significance was determined by one-way analysis of variance with Dunnetts post-test using the GraphPad Prism 5 software. Statistical significance between samples was indicated as follows *, p<0.05; , p<0.01; *, p<0.001.
Figure 6:
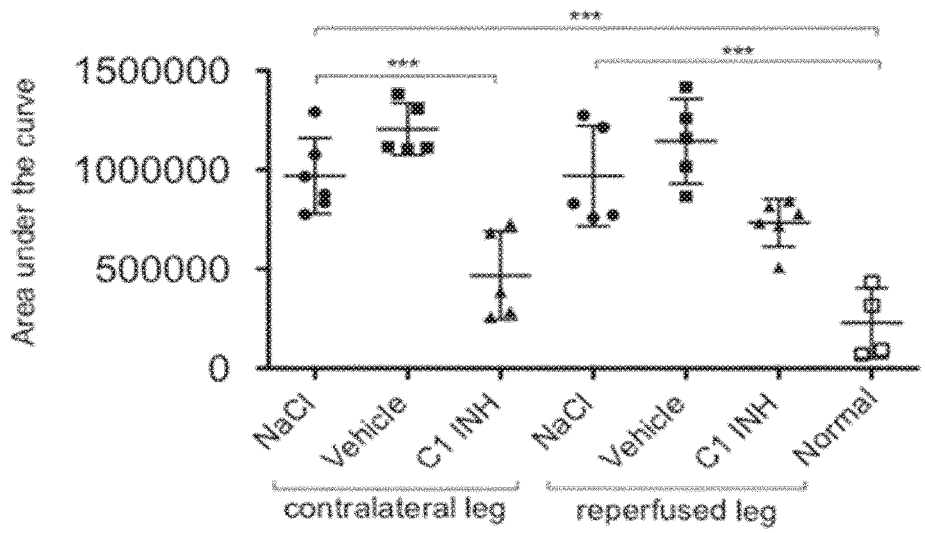

Complement Deposition was Inhibited by C1INH in the Contralateral Limb, Kidney and Liver The ischemic and the contralateral non-ischemic leg were analyzed for the deposition of complement fragments as markers for complement activation. As shown in FIGS. 6A and B, C1INH significantly reduced the deposition of C3b (classical and lectin pathway) as well as factor B (alternative pathway of complement activation) in the reperfused as well as in the contralateral leg. In addition treatment with C1INH caused a significant reduction of C3b deposition in the kidney, and of factor B deposition in the liver.

Treatment with C1INH Preserved the Endothelial Glycocalyx in the Contralateral Limb Healthy EC are covered by a layer of glycosaminoglycans as e.g. heparan sulfate (HS), which is crucial for the anti- Following cytokines could not be detected: IL-1β, IL-2, IL-6, IL-12p70, IL-13, G-CSF and GM-CSF. Data are expressed as means±SD. Statistical significance was determined by Student's t-test using the GraphPad Prism 5 software. P values of <0.05 were considered statistically significant.

Effect of C1INH Treatment on Apoptosis in Lung and Kidney Cortex

Apoptosis was assessed using TUNEL assay. Cells in lung tissue of the vehicle-treated animals showed a high degree of apoptosis (76±21%). In the cortex of kidneys, in proximal tubular epithelial cells, apoptosis was also observed in the vehicle-treated animals (43±25%). In comparison, C1INH-treated animals showed a significant reduction in apoptotic cells (10±12% in lung (P<0.0001) and 7±8% in kidney cortex).

iii) Effects of FXII Inhibitor rHA-Infestin-4 on IRI-Induced Remote Tissue and Organ Damage Treatment with rHA-Infestin-4 as described above also leads to a significant reduction in lung edema and potentially also reduces edema formation in other tissues.

In addition, a significant reduction in fibrin deposition in the lung (and potentially also in other tissues) is observed.

A significant reduction effect on apoptosis in lung and other tissues is observed after treatment with rHA-Infestin-4. rHA-Infestin-4 also leads to a reduction in the deposition of IgM and complement components, and potentially also shows an effect on the inflammatory cytokine and chemokine network.

REFERENCE LIST

1. Blaisdell, F. W. 2002. The pathophysiology of skeletal muscle ischemia and the reperfusion syndrome: a review. *Cardiovasc Surg* 10: 620-630.
2. Zeerleder, S. 2011. C1-inhibitor: more than a serine protease inhibitor. *Semin Thromb Hemost.* 37: 362-374.
3. Caliezi, C., W. A. Wuillemin, S. Zeerleder, M. Redondo, B. Eisele, and C. E. Hack. 2000. C1-Esterase inhibitor: an anti-inflammatory agent and its potential use in the treatment of diseases other than hereditary angioedema. *Pharmacol Rev* 52: 91-112.
4. Davis, A. E., III, P. Mejia, and F. Lu. 2008. Biological activities of C1 inhibitor. *Mol Immunol* 45: 4057-4063.
5. Nielsen, E. W., T. E. Mollnes, J. M. Harlan, and R. K. Winn. 2002. C1-inhibitor reduces the ischaemia-reperfusion injury of skeletal muscles in mice after aortic cross-clamping. *Scand J Immunol* 56: 588-592.
6. Toomayan, G. A., L. E. Chen, H. X. Jiang, W. N. Qi, A. V. Seaber, M. M. Frank, and J. R. Urbaniak. 2003. C1-esterase inhibitor and a novel peptide inhibitor improve contractile function in reperfused skeletal muscle. *Microsurgery* 23: 561-567.
7. Inderbitzin, D., G. Beldi, I. Avital, G. Vinci, and D. Candinas. 2004. Local and remote ischemia-reperfusion injury is mitigated in mice overexpressing human C1 inhibitor. *Eur Surg Res* 36: 142-147.
8. Dick, F., J. Li, M. N. Giraud, C. Kalka, J. Schmidli, and H. Tevaearai. 2008. Basic control of reperfusion effectively protects against reperfusion injury in a realistic rodent model of acute limb ischemia. *Circulation* 118: 1920-1928.
9. Bouillet, L. 2011. Icatibant in hereditary angioedema: news and challenges. *Expert Rev Clin Immunol* 7: 267-272.
10. Souza, D. G., E. S. Lomez, V. Pinho, J. B. Pesquero, M. Bader, J. L. Pesquero, and M. M. Teixeira. 2004. Role of bradykinin B2 and B1 receptors in the local, remote, and systemic inflammatory responses that follow intestinal ischemia and reperfusion injury. *J Immunol* 172: 2542-2548.
11. Johnson, G. B., G. J. Brunn, Y. Kodaira, and J. L. Platt. 2002. Receptor-mediated monitoring of tissue well-being via detection of soluble heparan sulfate by Toll-like receptor 4. *J Immunol* 168.
12. Platt, J. L., G. M. Vercellotti, B. J. Lindman, T. R. Oegema, Jr., F. H. Bach, and A. P. Dalmasso. 1990. Release of heparan sulfate from endothelial cells. Implications for pathogenesis of hyperacute rejection. *J Exp Med* 171.
13. Ihrcke, N. S., and J. L. Platt. 1996. Shedding of heparan sulfate proteoglycan by stimulated endothelial cells: evidence for proteolysis of cell-surface molecules. *J Cell Physiol* 168.
14. Ihrcke, N. S., W. Parker, K. J. Reissner, and J. L. Platt. 1998. Regulation of platelet heparanase during inflammation: role of pH and proteinases. *J Cell Physiol* 175.
15. Liu, D., F. Lu, G. Qin, S. M. Fernandes, J. Li, and A. E. Davis, III. 2007. C1 inhibitor-mediated protection from sepsis. *J Immunol* 179: 3966-3972.
16. Storini, C., E. Rossi, V. Marrella, M. Distaso, R. Veerhuis, C. Vergani, L. Bergamaschini, and M. G. De Simoni. 2005. C1-inhibitor protects against brain ischemia-reperfusion injury via inhibition of cell recruitment and inflammation. *Neurobiol. Dis* 19: 10-17.

The invention claimed is:

1. A method of ameliorating and/or reducing remote ischemia-reperfusion injury (IRI), comprising administering an effective dose of a Factor XII (FXII) inhibitor to an individual in need thereof,
wherein the FXII inhibitor is an antibody.

2. The method according to claim 1, wherein the antibody is administered parenterally to the individual.

3. The method according to claim 2, wherein the antibody is administered intravenously, intraarterially, or subcutaneously to the individual.

4. The method according to claim 1, wherein the antibody is administered to the individual at a dose ranging from 0.01 to 50 mg/kg body weight.

5. The method according to claim 1, wherein the individual is a patient and the antibody is administered before, during, and/or after a surgical intervention involving reperfusion.

6. The method according to claim 5, wherein the antibody is administered to the patient up to 6 hours before the surgical intervention or the start of reperfusion.

7. The method according to claim 5, wherein the antibody is administered to the patient within 72 hours after termination of the surgical intervention or the start of reperfusion.

8. The method according to claim 5, wherein the surgical intervention is chosen from the group consisting of (a) elective surgery, reconstructive surgery, vascular surgery, cardiac surgery, trauma surgery, crash or crush surgery, cancer surgery, orthopedic surgery, transplantation, and minimally invasive surgery, or the group consisting of (b) surgical intervention following onset of an initial thrombotic or thromboembolic or another ischemia-inducing disorder, insertion of a device for delivery of one or more pharmacologically active substances, insertion of a device for mechanical removal of complete or partial obstructions, and injection of pharmaceutically active substances.

9. The method according to claim 1, wherein the reperfusion happens spontaneously or through intervention other than a surgical intervention.

10. The method of claim 1, wherein the remote ischemia-reperfusion injury (IRI) affects one or more organs or tissues.

11. The method of claim 10, wherein the one or more organs or tissues is chosen from lung, heart, brain, kidney, intestine, pancreas, liver, extremities, and limbs.

12. The method of claim 1, wherein the remote ischemia-reperfusion injury (IRI) would lead to multiorgan dysfunction syndrome or systemic inflammatory response syndrome in the absence of treatment.

13. The method of claim 1, wherein the antibody is an anti-FXIIa monoclonal antibody.

14. The method of claim 13, wherein the anti-FXIIa monoclonal antibody comprises:
  a) a heavy chain variable region comprising a CDR1 domain comprising the amino acid sequence of SEQ ID NO: 9, a CDR2 domain comprising the amino acid sequence of SEQ ID NO: 11, and a CDR3 domain comprising the amino acid sequence of SEQ ID NO: 13; and
  b) a light chain variable region comprising a CDR1 domain comprising the amino acid sequence of SEQ ID NO: 14 or SEQ ID NO: 18, a CDR2 domain comprising the amino acid sequence of SEQ ID NO: 15, and a CDR3 domain comprising the amino acid sequence of SEQ ID NO: 17.

15. The method of claim 1, wherein the antibody comprises a heavy chain variable region comprising the amino acid sequence of SEQ ID NO: 7 and a light chain variable region comprising the amino acid sequence of SEQ ID NO: 8.

16. A method of ameliorating and/or reducing ischemia-reperfusion injury (IRI) in a patient that is to undergo a surgical intervention, comprising administering to the patient an effective dose of a Factor XII (FXII) inhibitor prior to and/or during and/or after the surgical intervention or prior to and/or after start of reperfusion, wherein the ischemia-reperfusion injury (IRI) affects an organ or tissue remote from the site of surgery, wherein the FXII inhibitor is an antibody.

17. The method of claim 16, wherein the remote ischemia-reperfusion injury (IRI) affects one or more organs or tissues chosen from lung, heart, brain, kidney, intestine, pancreas, liver, extremities, and limbs.

18. The method of claim 16, wherein the remote ischemia-reperfusion injury (IRI) would lead to multiorgan dysfunction syndrome or systemic inflammatory response syndrome in the absence of treatment.

19. The method of claim 16, wherein the antibody is an anti-FXIIa monoclonal antibody.

20. The method of claim 19, wherein the anti-FXIIa monoclonal antibody comprises:
  a) a heavy chain variable region comprising a CDR1 domain comprising the amino acid sequence of SEQ ID NO: 9, a CDR2 domain comprising the amino acid sequence of SEQ ID NO: 11, and a CDR3 domain comprising the amino acid sequence of SEQ ID NO: 13; and
  b) a light chain variable region comprising a CDR1 domain comprising the amino acid sequence of SEQ ID NO: 14 or SEQ ID NO: 18, a CDR2 domain comprising the amino acid sequence of SEQ ID NO: 15, and a CDR3 domain comprising the amino acid sequence of SEQ ID NO: 17.

21. The method of claim 16, wherein the antibody is a monoclonal anti-FXII antibody comprising a heavy chain variable region comprising the amino acid sequence of SEQ ID NO: 7 and a light chain variable region comprising the amino acid sequence of SEQ ID NO: 8.

* * * * *

UNITED STATES PATENT AND TRADEMARK OFFICE
CERTIFICATE OF CORRECTION

PATENT NO. : 10,973,891 B2  
APPLICATION NO. : 16/359598  
DATED : April 13, 2021  
INVENTOR(S) : Rolf Spirig et al.

Page 1 of 1

It is certified that error appears in the above-identified patent and that said Letters Patent is hereby corrected as shown below:

On the Title Page

In the Abstract:  
Item (57), Line 5, "inhibitory to an individual" should read --inhibitor to an individual--.

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*